(12) United States Patent
Dachs, II et al.

(10) Patent No.: US 9,095,362 B2
(45) Date of Patent: Aug. 4, 2015

(54) METHOD FOR PASSIVELY DECOUPLING TORQUE APPLIED BY A REMOTE ACTUATOR INTO AN INDEPENDENTLY ROTATING MEMBER

(75) Inventors: Gregory W. Dachs, II, San Francisco, CA (US); John W. Zabinski, Fremont, CA (US); Gabriel F. Brisson, Albany, CA (US); Todd Murphy, Palo Alto, CA (US)

(73) Assignee: INTUTITIVE SURGICAL OPERATIONS, INC., Sunnyvale, CA (US)

( * ) Notice: Subject to any disclaimer, the term of this patent is extended or adjusted under 35 U.S.C. 154(b) by 516 days.

(21) Appl. No.: 13/297,158

(22) Filed: Nov. 15, 2011

(65) Prior Publication Data
US 2012/0150192 A1 Jun. 14, 2012

Related U.S. Application Data

(60) Provisional application No. 61/413,885, filed on Nov. 15, 2010, provisional application No. 61/491,798, filed on May 31, 2011.

(51) Int. Cl.
*A61B 19/00* (2006.01)
*A61B 17/29* (2006.01)
*A61B 17/00* (2006.01)

(52) U.S. Cl.
CPC .............. *A61B 19/22* (2013.01); *A61B 19/2203* (2013.01); *A61B 2017/00477* (2013.01); *A61B 2017/2903* (2013.01); *A61B 2017/293* (2013.01);
(Continued)

(58) Field of Classification Search
CPC ............... A61B 19/22; A61B 19/2203; A61B 2019/2215; A61B 2019/2223; A61B 2019/2219; A61B 2019/2207; A61B 2019/2211; A61B 2019/2246; A61B 2019/2242; A61B 2017/2901; A61B 2017/2903; A61B 2017/2932; A61B 2017/293; A61B 2017/2938
See application file for complete search history.

(56) References Cited

U.S. PATENT DOCUMENTS 3,739,923 A 6/1973 Totsuka
3,784,031 A 1/1974 Niitu et al.
(Continued)

FOREIGN PATENT DOCUMENTS

EP 1982657 A2 10/2008
KR 100997196 B1 11/2010
(Continued)

OTHER PUBLICATIONS

International Search Report and Written Opinion for Application No. PCT/US2011/060849, mailed on Aug. 22, 2012, 21 pages.
(Continued)

*Primary Examiner* — Katherine Dowe
*Assistant Examiner* — Kendra Obu

(57) ABSTRACT

Surgical assemblies and related methods are disclosed that provide for the transmission of high levels of actuation torque to a rotary mechanism of an end effector supported by an independently rotatable main shaft without causing undesirable rotation of the main shaft. An input drive shaft is coupled with both the rotary mechanism and the main shaft via a transmission and a rotational coupling so that the main shaft is passively subjected to a counteracting torque opposite in direction to the actuation torque transmitted to the rotary mechanism so as to inhibit rotational driving of the main shaft by the transmitted actuation torque.

40 Claims, 22 Drawing Sheets

(52) U.S. Cl.
CPC . *A61B 2017/2936* (2013.01); *A61B 2017/2938* (2013.01); *A61B 2017/2943* (2013.01); *A61B 2019/2242* (2013.01)

(56) References Cited

U.S. PATENT DOCUMENTS

| | | | |
|---|---|---|---|
| 4,306,570 | A | 12/1981 | Matthews |
| 4,579,380 | A | 4/1986 | Zaremsky et al. |
| 4,903,536 | A | 2/1990 | Salisbury, Jr. |
| 5,458,387 | A | 10/1995 | Conway et al. |
| 5,895,084 | A | 4/1999 | Mauro |
| 7,044,706 | B2 | 5/2006 | Jung |
| 7,083,615 | B2 | 8/2006 | Petersen et al. |
| 7,373,219 | B2 | 5/2008 | Nowlin et al. |
| 7,386,365 | B2 | 6/2008 | Nixon |
| 7,918,230 | B2 | 4/2011 | Whitman et al. |
| 8,246,027 | B2 | 8/2012 | Li et al. |
| 8,534,729 | B2 | 9/2013 | Wilkinson et al. |
| 2007/0198008 | A1 | 8/2007 | Hauck et al. |
| 2008/0001559 | A1 | 1/2008 | Schena |
| 2008/0245175 | A1 | 10/2008 | Jinno et al. |
| 2009/0182193 | A1 | 7/2009 | Whitman et al. |
| 2010/0228250 | A1 | 9/2010 | Brogna |
| 2010/0228283 | A1 | 9/2010 | Jinno |
| 2010/0234866 | A1 | 9/2010 | Arcenio et al. |
| 2012/0150154 | A1 | 6/2012 | Brisson et al. |

FOREIGN PATENT DOCUMENTS

| | | |
|---|---|---|
| WO | WO-2009039506 A1 | 3/2009 |
| WO | WO-2010009473 A1 | 1/2010 |
| WO | WO-2011019206 A2 | 2/2011 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

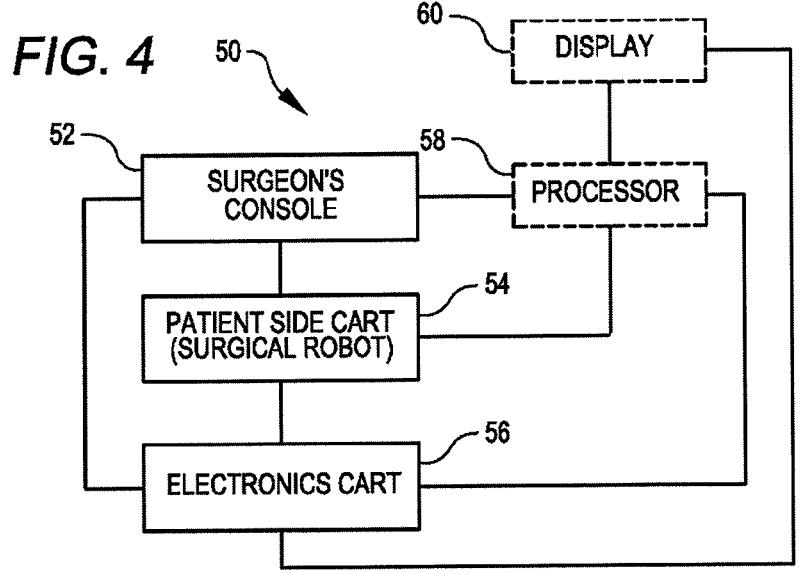
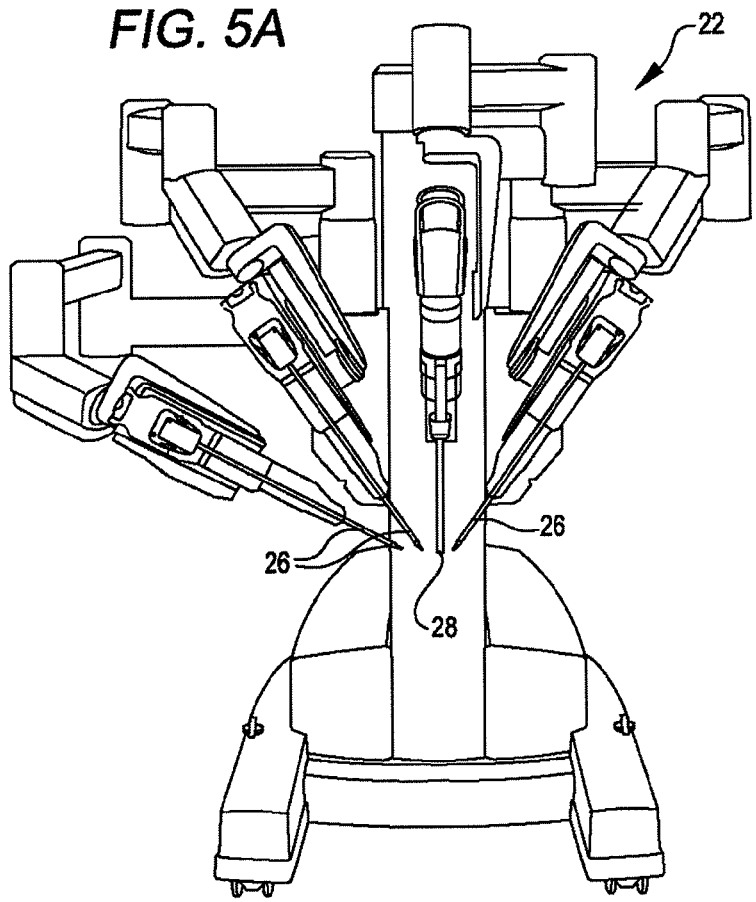

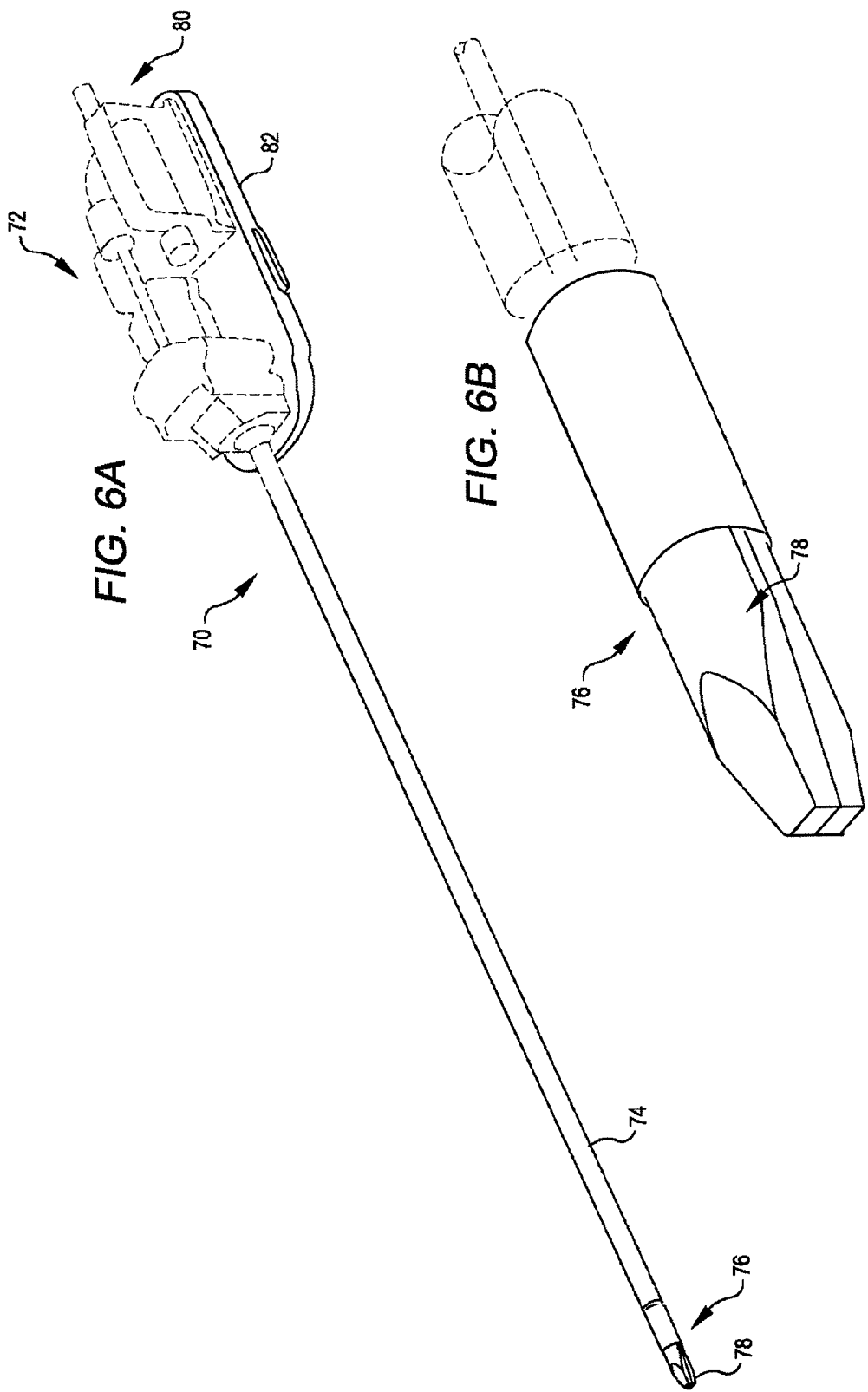

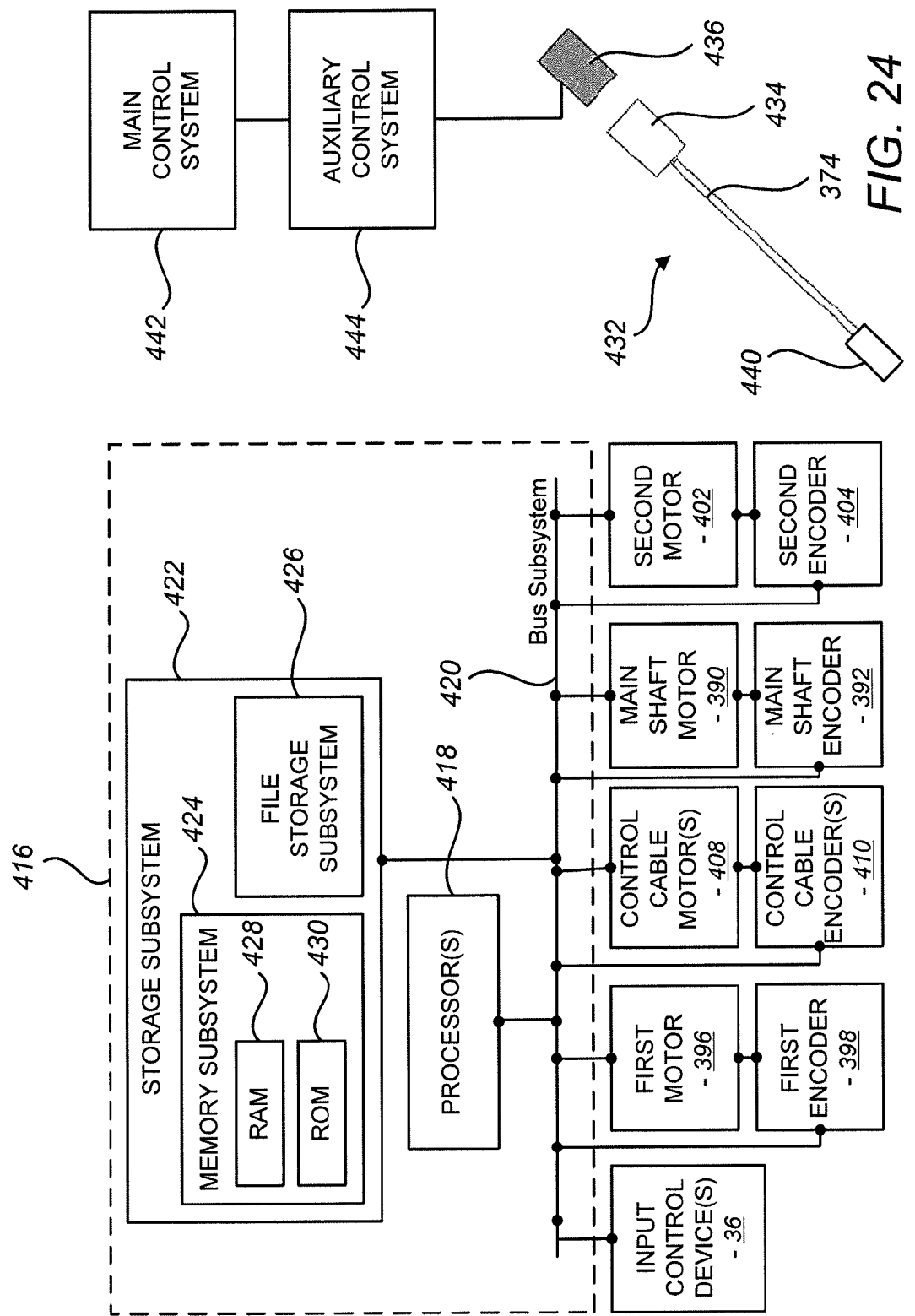

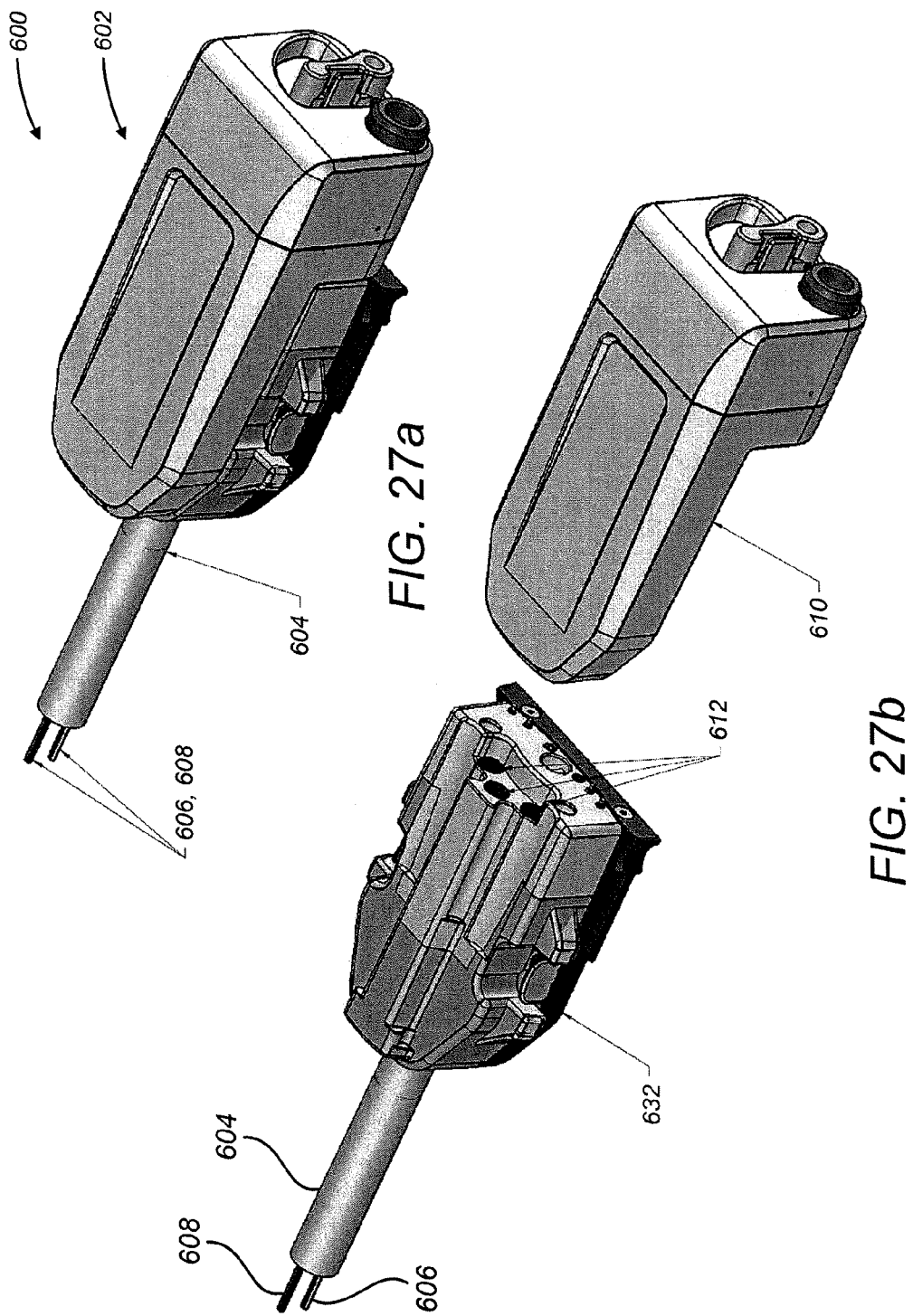

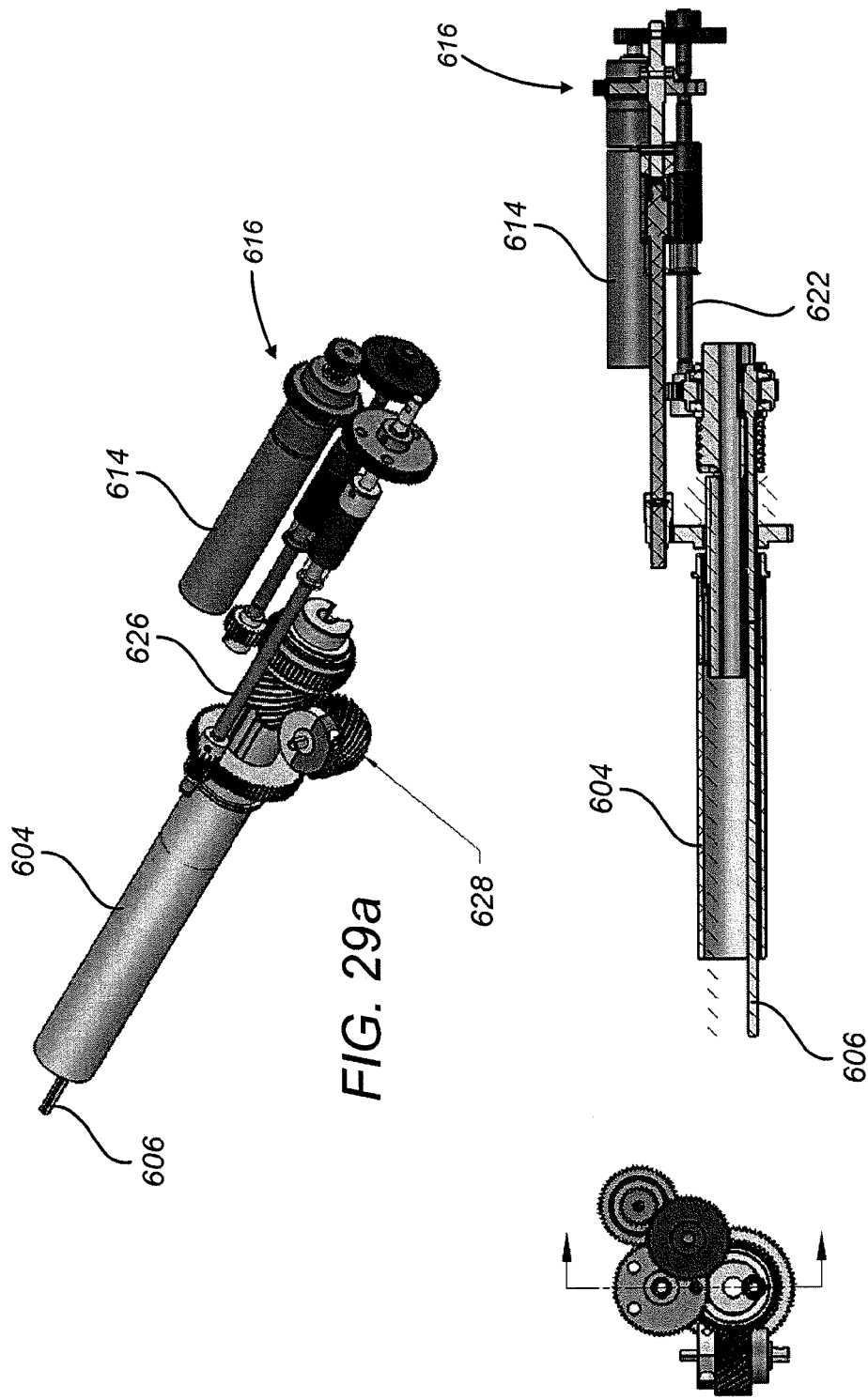

METHOD FOR PASSIVELY DECOUPLING TORQUE APPLIED BY A REMOTE ACTUATOR INTO AN INDEPENDENTLY ROTATING MEMBER

CROSS-REFERENCES TO RELATED APPLICATIONS

The present application claims the benefit of U.S. Provisional Application No. 61/413,885, entitled "METHOD FOR PASSIVELY DECOUPLING TORQUE APPLIED BY A REMOTE ACTUATOR INTO AN INDEPENDENTLY ROTATING MEMBER," filed on Nov. 15, 2010; and U.S. Provisional Application No. 61/491,789, entitled "DECOUPLING INSTRUMENT SHAFT ROLL AND END EFFECTOR ACTUATION IN A SURGICAL INSTRUMENT," filed on May 31, 2011; the full disclosures of which are incorporated herein by reference.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

In many existing minimally invasive telesurgical robotic systems, manipulation of the surgical instruments is provided by a surgical robot having a number of robotic arms. Each of the robotic arms has a number of robotic joints and a mounting fixture for the attachment of a surgical instrument. Integrated in with at least one of the mounting fixtures are a number of drive couplers (e.g., rotary drive couplers) that drivingly interface with corresponding input couplers of a surgical instrument. The surgical instrument includes mechanisms that drivingly couple the input couplers with an associated motion of the surgical instrument (e.g., main shaft rotation, end effector pitch, end effector yaw, end effector jaw clamping, deployment of staples, tissue cutting, etc.). In many existing minimally invasive telesurgical robotic systems, each of the drive couplers of the surgical robot are cable driven so as to, for example, provide for precise control over the movement of the output couplers as is possible in cable driven actuation systems. By precisely controlling the movement of the output couplers, precise control over the associated motions of the surgical instrument can be achieved.

A cable driven output coupler typically has a limited range of motion. Such a limited range of motion may not be detrimental where the output coupler is associated with a motion of the end effector that is not impacted by any other motion of the end effector. Such a limited range of motion may, however, be detrimental where the output coupler is associated with a motion of the end effector that is impacted by another motion of the end effector. For example, instrument shaft rotation may detrimentally couple with rotation of a drive shaft used to actuate an end effector mechanism (e.g., a clamping mechanism, a mechanism for the deployment of staples, a tissue cutting mechanism, etc.). Although compensating motions of the output couplers associated with the rotation of the instrument shaft and rotation of the drive shaft can be made, such compensating motions reduce the portion of the limited range of motion of the output couplers that can be used for their primary purpose.

Thus, there is believed to be a need for surgical assemblies and related methods for decoupling related motions of a surgical instrument, particularly decoupling instrument shaft roll and end effector actuation in a surgical instrument.

Manipulation and control of these effectors is also a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Non-robotic linear clamping, cutting and stapling devices have been employed in many different surgical procedures. For example, such a device can be used to resect a cancerous or anomalous tissue from a gastro-intestinal tract. Many known surgical devices, including known linear clamping, cutting and stapling devices, often have opposing jaws that are used to manipulate patient tissue.

For known devices having opposing jaws, a significant amount of mechanical power must be delivered to the end effector to effectively, for example, clamp tissue, staple tissue, cut tissue, etc. In most cases, the main shaft of the instrument must react at least a portion of mechanical forces and/or torques delivered to the end effector, whether via compression of the main shaft to react a tensile force or via torsion of the main shaft to react a torque delivered via a drive shaft disposed within the main shaft. If the main shaft or the mechanism used to rotationally position the main shaft, is not sufficiently rigid, the main shaft may move unexpectedly in response to the reacted force or torque.

Thus, there is also believed to be a need for a surgical assembly that transmits high actuation torque to an end effector that does not experience unintended rotation of an independently rotatable main shaft used to support the end effector due to the transmitted actuation torque.

BRIEF SUMMARY

Surgical assemblies and related methods are disclosed that provide for decoupling of instrument shaft roll and end effector actuation. In many embodiments, a differential is used to combine a motion associated with rotation of an instrument shaft with an input motion to generate an output motion to an actuation mechanism of an end effector supported by the distal end of the instrument shaft. The actuation mechanism articulates a portion of the end effector (e.g., a gripping jaw, a mechanism for the deployment of staples, a tissue cutting mechanism, etc.). The differential can be configured such that rotation of the instrument shaft results in substantially zero articulation of the end effector portion, thereby eliminating the possibility of any detrimental coupling between instrument shaft roll and end effector actuation.

Thus, in one aspect, a surgical assembly is provided. The surgical assembly includes a base, an instrument shaft rotationally mounted to the base and extending between a distal end and a proximal end, an end effector supported at the distal end of the instrument shaft and including an actuation mechanism driven by a rotational motion, a drive shaft rotationally coupled with the actuation mechanism and configured to provide the rotational motion to the actuation mechanism, and a differential rotationally coupled to the drive shaft and receiving a first input motion and a second input motion. The differential is configured to combine the first and second input motions to generate the rotational motion that rotates the drive shaft. The first input motion is rotationally coupleable to an actuation source. And the second input motion is coupled to rotation of the instrument shaft relative to the base. In many embodiments, the end effector includes a jaw articulated by the actuation mechanism.

The surgical assembly can be configured to substantially decouple actuation of the actuation mechanism from rotation of the instrument shaft. For example, the differential can be configured such that rotation of the instrument shaft relative to the base results in substantially zero rotation of the drive shaft relative to the instrument shaft when the first input motion is zero.

The differential can be implemented by using cables and pulleys. For example, the differential can include a first cable drivingly coupling rotation of the drive shaft relative to the base to rotation of the instrument shaft relative to the base and a second cable drivingly coupled to the actuation source. In many embodiments, the second cable is coupled to first and second pulley blocks having first and second pulleys, respectively, the first cable being engaged by the first and second pulleys. As another example, the differential can include a first cable drivingly coupling rotation of the drive shaft relative to the base to the actuation source and a second cable drivingly coupled to rotation of the instrument shaft relative to the base. In many embodiments, the second cable is coupled to first and second pulley blocks having first and second pulleys, respectively, the first cable being engaged by the first and second pulleys.

The differential can include a planetary gear box that includes a sun gear, planet gears coupled to a carrier, and a ring gear. In many embodiments, the first input motion rotates the carrier, the second input motion rotates the sun gear, and rotation of the ring gear is transferred to the drive shaft. The first input motion can be transferred to the carrier through an input shaft. And the sun gear can rotate around the input shaft. In many embodiments, the input shaft is oriented transverse to the instrument shaft. The surgical assembly can include a torsion spring coupled between the base and the carrier to return the drive shaft to a predetermined rotational position relative to the instrument shaft upon a disconnection between the actuation source and the carrier.

In another aspect, a method is provided of decoupling rotation of a surgical instrument shaft from rotation of a drive shaft drivingly coupled with a mechanism of an end effector. The method includes generating a first input motion associated with a desired end effector configuration; rotating the surgical instrument shaft relative to a base, the surgical instrument shaft extending between a proximal end adjacent to the base and a distal end that supports the end effector; generating a second input motion in response to the rotation of the surgical instrument shaft relative to the base; combining the first and second input motions to generate an output motion; and rotating the drive shaft in response to the output motion. In many embodiments, the first and second input motions are combined such that no substantial rotation of the drive shaft relative to the surgical instrument shaft occurs when the first input motion is zero.

The method can be implemented by using cables. For example, the method can include moving a first cable in response to the rotation of the surgical instrument shaft relative to the base, moving a second cable, moving a first pulley and a second pulley in response to the movement of the second cable, engaging the first cable with each of the first and second pulleys, and rotating the drive shaft in response to movement of the first cable. In many embodiments, the method includes engaging the first cable with each of the first and second pulleys over an approximately 180 degree sector of the respective pulley. As another example, the method can include moving a first cable, moving a second cable in response to the rotation of the surgical instrument shaft relative to the base, moving a first pulley and a second pulley in response to the movement of the second cable, engaging the first cable with each of the first and second pulleys, and rotating the drive shaft in response to movement of the first cable. In many embodiments, the method includes engaging the first cable with each of the first and second pulley over an approximately 180 degree sector of the respective pulley.

The method can be implemented by using a differential gear assembly. For example, the method can include rotating a first input link of a differential gear assembly in response to the first input motion, rotating a second input link of the differential gear assembly in response to the second input motion, and rotating the drive shaft in response to rotation of an output link of the differential gear assembly. In many embodiments, the differential gear assembly includes a planetary gear assembly having a sun gear, planet gears coupled to a carrier, and a ring gear. Any suitable coupling of the first and second input motions to the differential can be used. For example, the first input motion can rotate the carrier, the second input motion can rotate the sun gear, and the output motion can be generated by rotation of the ring gear. The method can include transferring the first input motion to the carrier through an input shaft, and rotating the sun gear around the input shaft. In many embodiments, the input shaft is oriented transverse to the instrument shaft. The method can include returning the end effector mechanism to a predetermined configuration upon a disconnect between an actuation source generating the first input motion and the first input link of the differential gear assembly.

Surgical assemblies and related methods are also disclosed that provide for the transmission of high levels of actuation torque to a rotary mechanism of an end effector supported by an independently rotatable main shaft without causing undesirable rotation of the main shaft. An input drive shaft is coupled with both the rotary mechanism and the main shaft via a transmission and a rotational coupling so that the main shaft is passively subjected to a counteracting torque opposite in direction to the actuation torque transmitted to the rotary mechanism so as to inhibit unintended rotation (e.g., back driving) of the main shaft. The disclosed assemblies and methods can be expanded to transmit high levels of actuation torque to two or more rotary mechanisms of an end effector while passively inhibiting unintended rotation of the main shaft. The disclosed assemblies and methods can be particularly advantageous when employed in minimally invasive robotic surgical assemblies and procedures.

Thus, in another aspect, a minimally invasive robotic surgical assembly is provided. The surgical assembly includes a base; a main shaft assembly rotationally mounted to the base, the main shaft assembly including a main shaft, an end effector supported by the main shaft, and a first end effector drive shaft drivingly coupled to the end effector; a main shaft drive rotationally driving the main shaft relative to the base; a first input drive shaft transmitting a first input torque; and a first transmission having a first input link rotationally coupled to the first drive shaft, a first output link rotationally coupled to the first end effector drive shaft, and a first base link. The first transmission provides a first gear ratio between the first input link and the first output link so as to transmit a first output torque to the main shaft assembly in response to the first input torque. A first end effector torque is transmitted by the first end effector drive shaft to the end effector in response to the first output torque. The first base link is rotationally coupled with the main shaft by a second gear ratio such that the first base link, in response to the first input torque, transmits a first counteracting torque to the main shaft that is opposite in direction from the first output torque. The first counteracting torque inhibits rotational driving of the main shaft assembly by the first output torque. The first output link can be coupled with the first end effector drive shaft via a rotational coupling providing a non-unity gear ratio.

In many embodiments, the magnitude of the first counteracting torque is at least roughly equivalent to the magnitude of the first output torque. Preferably, the magnitude of the first counteracting torque is within 10 percent of the magnitude of the first output torque. And ideally, the magnitude of the first counteracting torque is within 2 percent of the magnitude of the first output torque.

In many embodiments, the main shaft assembly has a back-driving torque threshold such that the main shaft back drives the main shaft drive when the main shaft is subject to a net torque over the back-driving torque threshold and does not back drive the main shaft drive when the main shaft is subject to a net torque under the back-driving torque threshold. The magnitude of the first counteracting torque can differ from the magnitude of the first output torque by a first net torque that is less than the back-driving torque threshold. Preferably, the first net torque magnitude is less than 50 percent of the back-driving torque threshold. More preferably, the first net torque magnitude is less than 25 percent of the back-driving torque threshold. More preferably still, the first net torque magnitude is less than 10 percent of the back-driving torque threshold. And ideally, the first net torque magnitude is less than 2 percent of the back-driving torque threshold.

In many embodiments, the first transmission includes a first planetary gear box having a first sun gear, a first ring gear, and first planetary gears supported by a first carrier. In many embodiments, the first sun gear corresponds to the first input link, the first carrier corresponds to the first output link, and the first ring gear corresponds to the first base link. In many embodiments, the first carrier corresponds to the first input link, the first sun gear corresponds to the first output link, and the first ring gear corresponds to the first base link. In many embodiments, the first sun gear or the first carrier correspond to the first base link.

In many embodiments, a rotation of the main shaft induces only a relatively small amount of rotation of the first end effector drive shaft relative to the main shaft. For example, in many embodiments a rotation of the main shaft induces a rotation of the first end effector drive shaft that is less than 10 percent of the rotation of the main shaft. And in many embodiments, the induced rotation of the first end effector drive shaft is less than 5 percent of the rotation of the main shaft.

In many embodiments, the surgical assembly further includes a second end effector drive shaft drivingly coupled to the end effector and included in the main shaft assembly; a second input drive shaft transmitting a second input torque; and a second transmission having a second input link rotationally coupled to the second input drive shaft, a second output link rotationally coupled to the second end effector drive shaft, and a second base link. The second transmission provides a third gear ratio between the second input link and the second output link so as to transmit a second output torque to the main shaft assembly in response to the second input torque. A second end effector torque is transmitted by the second end effector drive shaft to the end effector in response to the second output torque. The second base link is rotationally coupled with the main shaft by a fourth gear ratio such that the second base link, in response to the second input torque, transmits a second counteracting torque to the main shaft that is opposite in direction from the second output torque. The second counteracting torque inhibits rotational driving of the main shaft assembly by the second output torque. The second output link can be coupled with the second end effector drive shaft via a rotational coupling providing a non-unity gear ratio. And the surgical assembly can include a common drive shaft through which the first and second base links are rotationally coupled with the main shaft.

In many embodiments, the magnitude of the second counteracting torque is at least roughly equivalent to the magnitude of the second output torque. Preferably, the magnitude of the second counteracting torque is within 10 percent of the magnitude of the second output torque. And ideally, the magnitude of the second counteracting torque is within 2 percent of the magnitude of the second output torque.

In many embodiments, the main shaft assembly has a back-driving torque threshold such that the main shaft back drives the main shaft drive when the main shaft assembly is subject to a net torque over the back-driving torque threshold and does not back drive the main shaft drive when the main shaft assembly is subject to a net torque under the back-driving torque threshold. The magnitude of the second counteracting torque can differ from the magnitude of the second output torque by less than the back-driving torque threshold. Preferably, the second net torque magnitude is less than 50 percent of the back-driving torque threshold. More preferably, the second net torque magnitude is less than 25 percent of the back-driving torque threshold. And ideally, the second net torque magnitude is less than 10 percent of the back-driving torque threshold.

In many embodiments, the second transmission includes a second planetary gear box having a second sun gear, a second ring gear, and second planetary gears supported by a second carrier. In many embodiments, the second sun gear corresponds to the second input link, the second carrier corresponds to the second output link, and the second ring gear corresponds to the second base link. In many embodiments, the second carrier corresponds to the second input link, the second sun gear corresponds to the second output link, and the second ring gear corresponds to the second base link. In many embodiments, the second carrier or the second sun gear correspond to the second base link.

In another aspect, a method is provided for preventing an actuation torque transmitted to an end effector from back driving a back-drivable main shaft during surgery. The method includes rotating a first input link of a first transmission providing a first gear ratio between the first input link and a first output link of the first transmission. The first output link is rotationally coupled with a main shaft assembly rotationally mounted to a base and including a main shaft and an end effector supported by the main shaft. A first output torque is transmitted by the first output link to the main shaft assembly and a first end effector torque is transmitted to the end effector in response to the first output torque. The first output torque is greater than a back-driving torque threshold for the main shaft assembly. The method further includes transmitting torque from a first base link of the first transmission through a first rotational coupling between the first base link and the main shaft. The first rotational coupling provides a second gear ratio between the first base link and the main shaft such that a first counteracting torque is applied to the main shaft that is opposite in direction from the first output torque. The first counteracting torque inhibits rotational driving of the main shaft assembly by the first output torque.

The magnitude of the first counteracting torque can differ from the magnitude of the first output torque by a first net torque magnitude that is less than the back-driving torque threshold. Preferably, the first net torque magnitude is less than 50 percent of the back-driving torque threshold. More preferably, the first net torque magnitude is less than 25 percent of the back-driving torque threshold. And ideally, the first net torque magnitude is less than 10 percent of the back-driving torque threshold.

In many embodiments, the magnitude of the first counteracting torque is at least roughly equivalent to the magnitude of the first output torque. Preferably, the magnitude of the first counteracting torque is within 10 percent of the magnitude of the first output torque. And ideally, the magnitude of the first counteracting torque is within 2 percent of the magnitude of the first output torque.

In many embodiments, a first end effector drive shaft transmits the first end effector torque to the end effector and a rotation of the main shaft induces only a relatively small amount of rotation of the first end effector drive shaft. For example, in many embodiments a rotation of the main shaft induces a rotation of the first end effector drive shaft that is less than 10 percent of the rotation of the main shaft. And in many embodiments, the induced rotation of the first end effector drive shaft is less than 5 percent of the rotation of the main shaft.

In many embodiments, the method further includes rotating a second input link of a second transmission providing a third gear ratio between the second input link and a second output link of the second transmission. The second output link is rotationally coupled with the main shaft assembly so that a second output torque is transmitted by the second output link to the main shaft assembly and a second end effector torque is transmitted to the end effector in response to the second output torque. The second output torque is greater than the back-driving torque threshold. In many embodiments, the method further includes transmitting torque from a second base link of the second transmission through a second rotational coupling between the second base link and the main shaft. The second rotational coupling provides a fourth gear ratio between the second base link and the main shaft such that a second counteracting torque is applied to the main shaft that is opposite in direction from the second end output torque. The second counteracting torque inhibits rotational driving of the main shaft assembly by the second output torque. And in many embodiments, the first and second rotational couplings share a common drive shaft.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4 diagrammatically illustrates a robotic surgery system, in accordance with many embodiments.

FIG. 5A is a front view of a patient side cart (surgical robot) of a robotic surgery system, in accordance with many embodiments.

FIG. 6A is a perspective view of a robotic surgery tool that includes an end effector having opposing clamping jaws, in accordance with many embodiments.

FIG. 6B is a close-up perspective view of the end effector of FIG. 6A.

FIG. 23 diagrammatically illustrates the integration of components of the robotic assembly of FIG. 22 with a controller, in accordance with many embodiments.

FIG. 24 diagrammatically illustrates a robotic tool and an associated robotic system, in accordance with many embodiments.

FIG. 27a is a perspective view of a minimally-invasive surgical instrument assembly that includes drive motors coupled with an independently rotatable main shaft and respective internal drive shafts so as to avoid unintended rotation of the main shaft due to actuation torques transferred to the end effector by the drive shafts, in accordance with many embodiments.

FIG. 27b is an exploded perspective view of the instrument assembly of FIG. 27a illustrating a motor pack and drive couplings that couple drive motors in the motor pack to the main shaft and to the respective internal drive shafts.

FIG. 29a is a perspective view illustrating internal components of FIG. 29a associated with coupling one of the drive motors to the main shaft and the respective internal drive shaft.

FIG. 29b is an end view of the internal components of FIG. 29a.

FIG. 29c illustrates cross section A-A of FIG. 29b.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
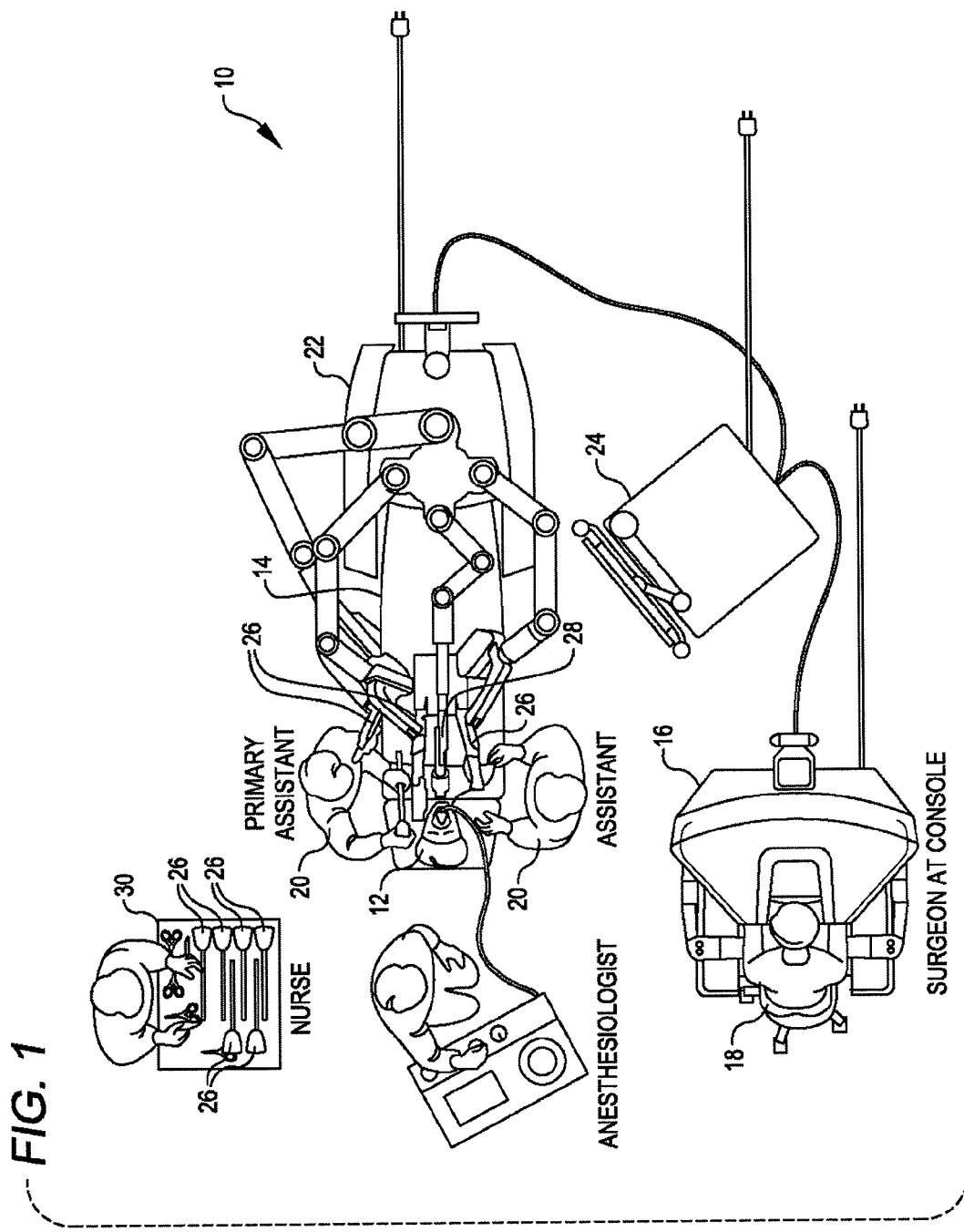
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
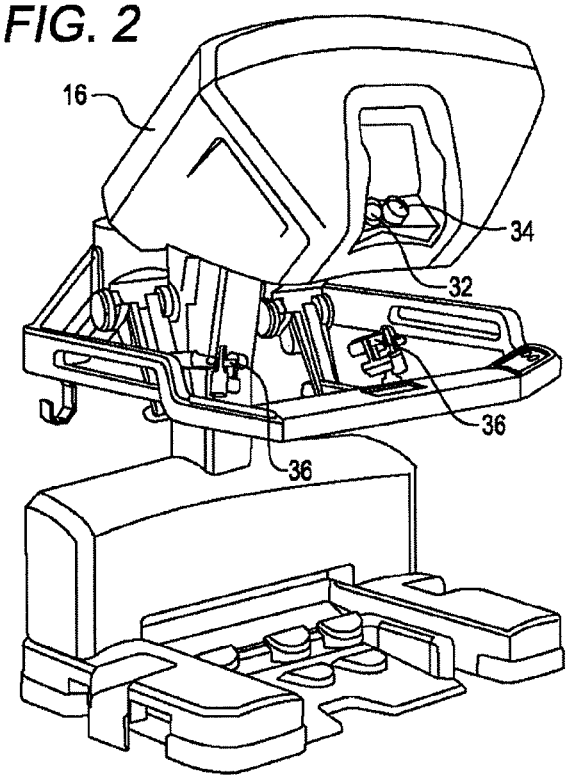
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
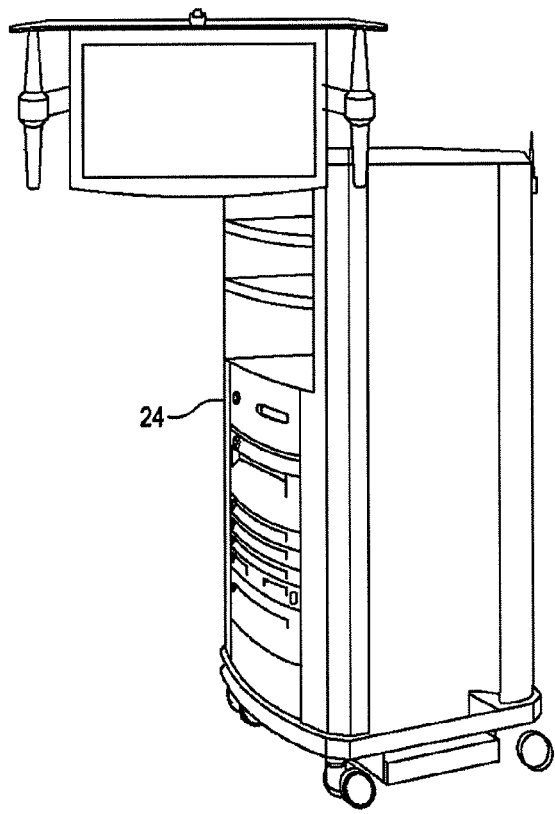
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5B:
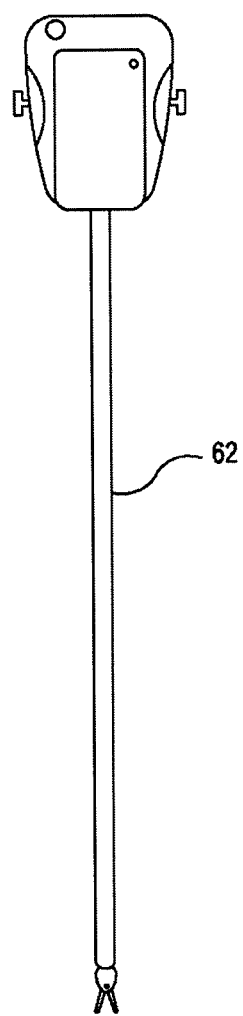
FIG. 5B is a front view of a robotic surgery tool.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Tissue Gripping End Effectors

FIG. 6A shows a surgical tool 70 that includes a proximal chassis 72, an instrument shaft 74, and a distal end effector 76 having a jaw 78 that can be articulated to grip a patient tissue. The proximal chassis includes an input coupler that is configured to interface with and be driven by an output coupler of the Patient Side Cart 22. The input coupler is drivingly coupled with an input link of a spring assembly 80. The spring assembly 80 is mounted to a frame 82 of the proximal chassis 72 and includes an output link that is drivingly coupled with a drive shaft that is disposed within the instrument shaft 74. The drive shaft is drivingly coupled with the jaw 78. FIG. 6B provides a close-up view of the jaw 78 of the end effector 76.

Figure 7:
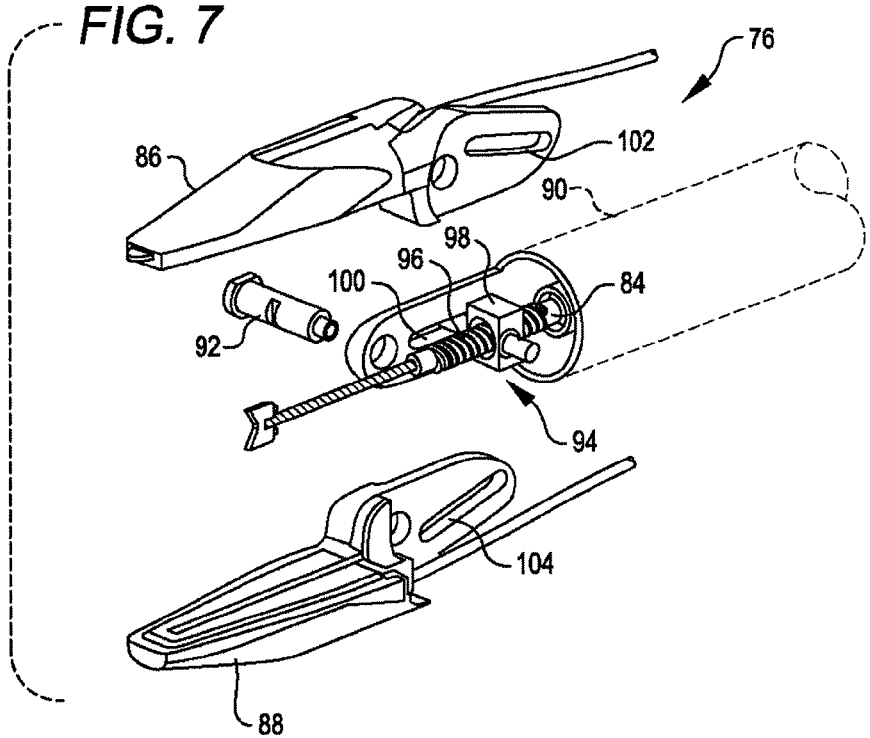
FIG. 7 is an exploded perspective view of the end effector of FIG. 6A, illustrating a mechanism used to convert rotary motion of a drive shaft into articulation of the opposing clamping jaws.

FIG. 7 is an exploded perspective view of the end effector 76 of FIG. 6A, illustrating a clamping mechanism used to convert rotary motion of a drive shaft 84 into articulation of opposing clamping jaws of the end effector 76. The end effector includes an upper jaw 86, a lower jaw 88, a frame 90, a pin 92 for pivotally mounting the upper jaw 86 and the lower jaw 88 to the frame 90, and a lead screw mechanism 94 that is drivingly coupled with the drive shaft 84. The lead screw mechanism 94 includes a lead screw 96 and a mating translating nut 98 that is advanced and retracted along a slot 100 in the frame 90 via rotation of the lead screw 96. The translating nut 98 includes oppositely extending protrusions that interface with a slot 102 in the upper jaw 86 and with a slot 104 in the lower jaw 88, thereby causing articulation of the upper jaw 86 and the lower jaw 88 about the pin 92 when the translating nut 98 is advanced or retracted along the slot 100.

Figure 8A:
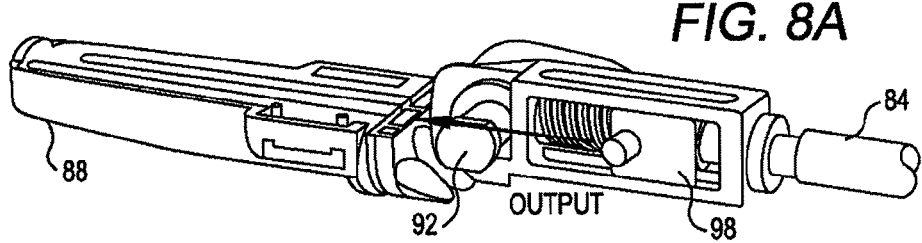
FIGS. 8A and 8B are perspective views of an end effector having opposing clamping jaws and a mechanism used to convert rotary motion of a drive shaft into articulation of the opposing clamping jaws, in accordance with many embodiments.
Figure 8B:
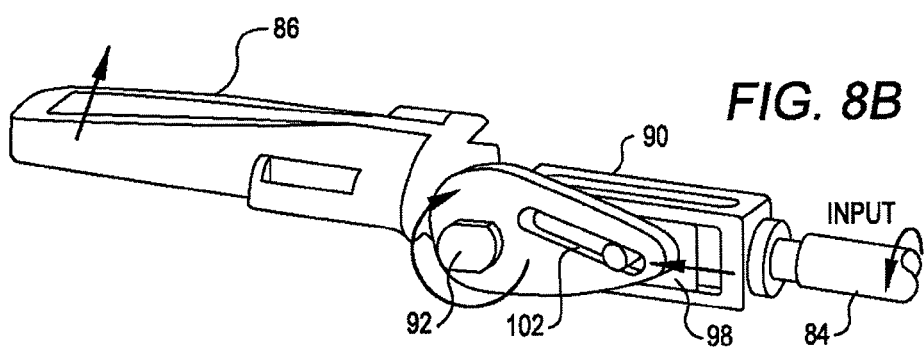

FIG. 8A and FIG. 8B illustrate the operation of a clamping mechanism similar to the clamping mechanism of FIG. 7. Rotating the drive shaft 84 in the direction shown causes a translating nut 98 to advance distally toward the pivot pin 92 by which the lower jaw 88 and the upper jaw 86 are pivotally mounted to the frame 90 of an end effector. As illustrated in FIG. 8B, a protrusion of the translating nut 98 engages the slot 102 in the upper jaw 86. Distal advancement of the translating nut 98 toward the pivot pin 92 causes the upper jaw to rotate in the direction shown, and causes the lower jaw 88 to rotate in the opposite direction, thereby opening the jaw. Similarly, proximal advancement of the translating nut 98 away from the pivot pin 92 cause the jaw to close. Accordingly, the jaw can be articulated to grip a patient tissue.

The lead screw type clamping mechanisms shown in FIG. 7, FIG. 8A, and FIG. 8B provide a substantial mechanical advantage, which converts a relatively low torque transmitted by the drive shaft into a relatively high clamping force. To avoid subjecting tissue to an excessive clamping force via a mechanism having such a substantial mechanical advantage, the torque transmitted into the clamping mechanism by the drive shaft can be controlled.

Alternate End Effector Mechanisms

The drive shaft 84 can be used to actuate any suitable end effector mechanism. For example, the drive shaft 84 can be used to actuate mechanisms such as a tissue stapling mechanism, a tissue cutting mechanism, and in general any suitable end effector mechanism that can be actuated by a rotational input.

Decoupling Instrument Shaft Roll and End Effector Actuation

Figure 9:
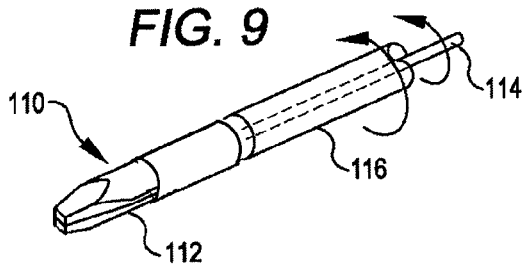
FIG. 9 is a simplified perspective view illustrating a drive shaft drivingly coupled with an actuation mechanism of an end effector that is supported at the distal end of a rotatable instrument shaft, in accordance with many embodiments.

FIG. 9 provides an appropriate starting point for discussing decoupling of instrument shaft roll and end effector actuation in a surgical instrument. FIG. 9 shows an end effector 110 that includes an articulated jaw 112 operable to grip an item (e.g., patient tissue, a suture needle, etc.). The end effector 110 includes an actuation mechanism for actuating a mechanism of the end effector 110, such as the articulated jaw 112. The actuation mechanism is drivingly coupled with a drive shaft 114. The end effector 110 is supported at a distal end of an instrument shaft 116. The instrument shaft 116 is rotatable through a range of rotation relative to a proximal chassis base that supports the instrument shaft 116. Likewise, the drive shaft 114 is rotatable through a range of rotation relative to the proximal chassis base.

Where the drive shaft 114 is driven independent of any tie to rotation of the instrument shaft 116, the portion of the range of rotation of the drive shaft 114 relative to the proximal chassis base that can be used to actuate the end effector jaw 112 is reduced by the range of rotation of the instrument shaft 116 relative to the proximal chassis base. For example, for a range of rotation of the instrument shaft 116 relative to the base equal to two revolutions and a range of rotation of the drive shaft 114 relative to the base equal to ten revolutions, the net range of rotation of the drive shaft 114 relative to the end effector 110 is equal to eight revolutions. In other words, two of the revolutions of the drive shaft 114 relative to the base are effectively negated by the two revolutions of the instrument shaft 116 relative to the base since these two separate two revolutions, when combined, produce zero net rotation of the drive shaft 114 relative to the actuation mechanism of the end effector 110.

Figure 10:
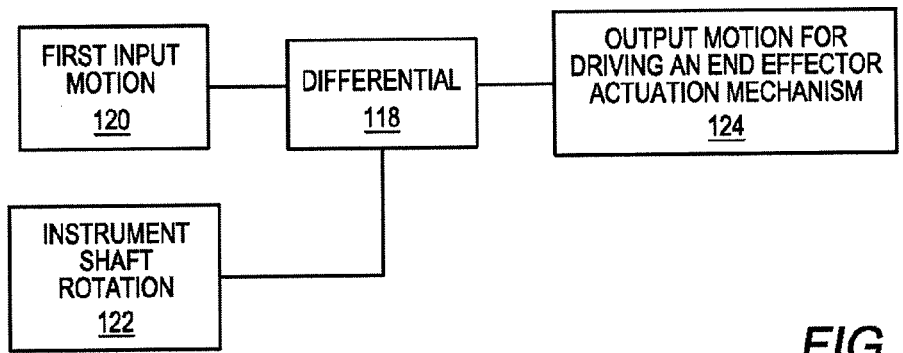
FIG. 10 is a simplified schematic illustrating the use of a differential to combine a first input motion with instrument shaft rotation to generate an output motion used to actuate an end effector mechanism, in accordance with many embodiments.

FIG. 10 schematically illustrates the use of a differential 118 for combining a first input motion 120 with an instrument shaft rotation 122 to generate an output motion 124 for driving an end effector actuation mechanism. The differential 118 can be configured to counteract the above-discussed impact of instrument shaft rotation on producing a difference between the amount of rotation of the drive shaft 114 relative to the proximal chassis base and the corresponding amount of rotation of the drive shaft 114 relative to the end effector actuation mechanism. For example, the differential 118 can be configured to combine a first input motion 120 of two clockwise revolutions relative to the proximal chassis base with an instrument shaft motion 122 of one clockwise revolution relative to the proximal chassis base to produce an output motion 124 of three clockwise revolutions relative to the proximal chassis base, which effectively provides an output motion of two clockwise revolutions relative to the end effector. Such a differential configuration also serves to counteract the above-discussed impact of instrument shaft rotation when the drive shaft 114 and the instrument shaft 116 are rotated in opposite directions. For example, with such a differential configuration, two clockwise revolutions of the first input motion 120 relative to the proximal chassis base combine with one counter-clockwise revolution of the instrument shaft 122 relative to the base to produce an output motion 124 of one clockwise revolution relative to the base, which effectively produces an output motion of two clockwise revolutions of the output motion relative to the end effector.

While it is preferred that the differential be configured to substantially counteract all of the above-discussed impact of instrument shaft rotation on producing a difference between the amount of rotation of the drive shaft relative to the proximal chassis base and the corresponding amount of rotation of the drive shaft relative to the end effector actuation mechanism, the differential can also be configured to counteract the impact of instrument shaft rotation to any suitable degree. For example, the differential can be configured to under counteract, over counteract, and even magnify the impact of the above-discussed impact of instrument shaft rotation as suitable for achieving desired operational characteristics of the surgical instrument.

The differential can be implemented in any suitable way. For example, the differential can be implemented using cables and pulleys. As another example, the differential can be implemented using gearing, such as a planetary gear box assembly.

Cable Implemented Differentials

Figure 11A:
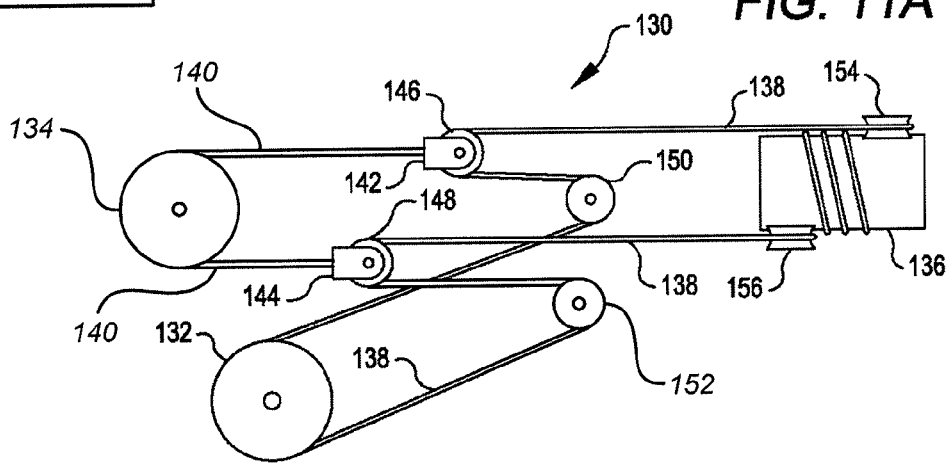
FIG. 11A is a simplified plan-view schematic illustrating a cable implemented differential used to decouple instrument shaft roll and end effector actuation in a surgical instrument, in accordance with many embodiments.

FIG. 11A illustrates a cable implemented differential 130 used to decouple instrument shaft roll and end effector actuation in a robotic surgical instrument, in accordance with many embodiments. The differential 130 includes a roll pulley 132 that is rotationally coupled with rotation of an instrument shaft relative to a proximal chassis base, an end effector actuation pulley 134 that is rotationally coupled with an actuation source, and a lead-screw drive pulley 136 that is rotationally coupled with an end effector jaw actuation mechanism. A first cable 138 that engages both the roll pulley 132 and the lead-screw drive pulley 136 provides for rotation of the lead-screw drive pulley 136 in response to rotation of the roll pulley 132. A second cable 140 that engages the end effector actuation pulley 134 is coupled with a first pulley block 142 and a second pulley block 144. The first pulley block 142 includes a first moving pulley 146. And the second pulley block 144 includes a second moving pulley 148. The first and second moving pulleys 146, 148 engage the first cable 138.

Between the roll pulley 132 and the lead-screw drive pulley 136, the first cable 138 engages four fixed guide pulleys. These fixed guide pulleys include a first guide pulley 150, a second guide pulley 152, a third guide pulley 154, and a fourth guide pulley 156.

Figure 11B:
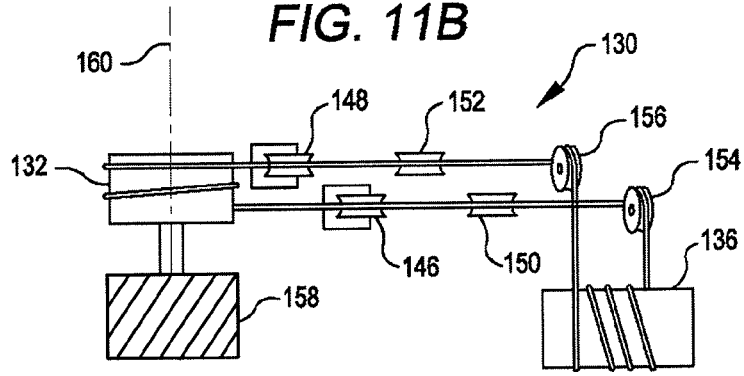
FIG. 11B is a simplified side-view schematic illustrating the cable implemented differential of FIG. 11A.

FIG. 11B is a side view of the cable implemented differential 130. The roll pulley 132 is rotationally coupled with rotation of the instrument shaft through a helical gear 158. The roll pulley 132 and the helical gear 158 rotate about an axis of rotation 160. The instrument shaft rotates about an axis of rotation that is oriented transverse to the helical gear axis of rotation 160. The helical gear 158 and a mating helical gear attached to rotate with the instrument shaft transfer rotation of the instrument shaft to rotation of the roll pulley 132.

The four fixed guide pulleys 150, 152, 154, 156 serve to constrain the location of the first cable 138 both horizontally and vertically. The first and third guide pulleys 150, 154 are positioned below the second and fourth guide pulleys 152, 156 to provide vertical separation between overlapping portions of the first cable 138. The first and third guide pulleys 150, 154 are also positioned horizontally to provide for a 180 degree engagement between the first moving pulley 146 and the first cable 138 throughout the range of travel of the first moving pulley 146. Likewise, the second and fourth guide pulleys 152, 156 are also positioned horizontally to provide for a 180 degree engagement between the second moving pulley 148 and the first cable 138 throughout the range of travel of the second moving pulley 148.

The cable implemented differential 130 combines the motion of the roll pulley 132 and the motion of the end effector actuation pulley 134 to produce motion of the lead-screw drive pulley 136. For example, in the absence of any rotation of the end effector actuation pulley 134, rotation of the roll pulley 132 produces a corresponding rotation of the lead-screw drive pulley 136, thereby resulting in no net rotation of the lead-screw drive pulley 136 relative to the end effector jaw actuation mechanism. In the absence of any rotation of the roll pulley 132, rotation of the end effector actuation pulley 134 produces a corresponding motion of the first and second moving pulleys 146, 148, thereby producing rotation of the lead-screw pulley 136. And for simultaneous rotation of both the roll pulley 132 and the end effector actuation pulley 134, the corresponding movements of the first cable 138 and the second cable 140 result in a rotation of the lead-screw drive pulley 136 that is a combination of the rotation of the roll pulley 132 and the end effector actuation pulley 134.

Figure 12:
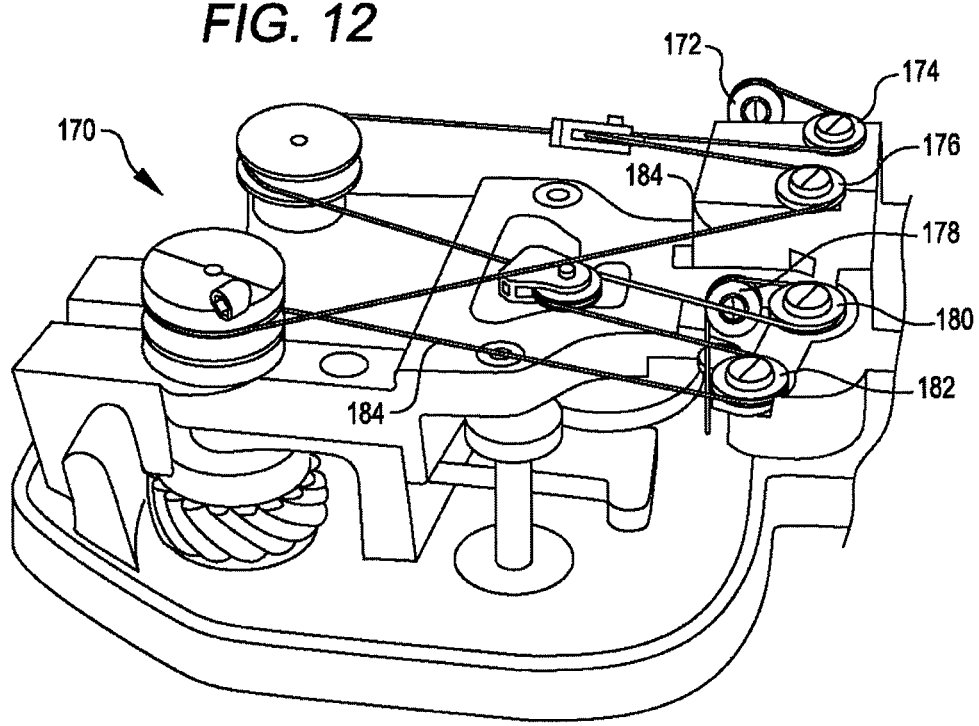
FIG. 12 is a perspective view illustrating a proximal chassis of a surgical instrument having a cable-driven differential used to decouple instrument shaft roll and end effector actuation in a surgical instrument, in accordance with many embodiments.

FIG. 12 is a perspective view of a proximal chassis of a robotic surgical instrument having a cable implemented differential 170, in accordance with many embodiments. The cable implemented differential 170 is configured similar to the cable implemented differential 130, but includes six fixed guide pulleys 172, 174, 176, 178, 180, 182 to constrain a first cable 184 horizontally and vertically.

Any suitable cable implemented differential can be used. For example, in a variation of the cable implemented differential 130, the first cable 138 is driven by the end effector actuation pulley 134 and the second cable 140 is driven by the roll pulley 132.

Gear Implemented Differentials

Figure 13:
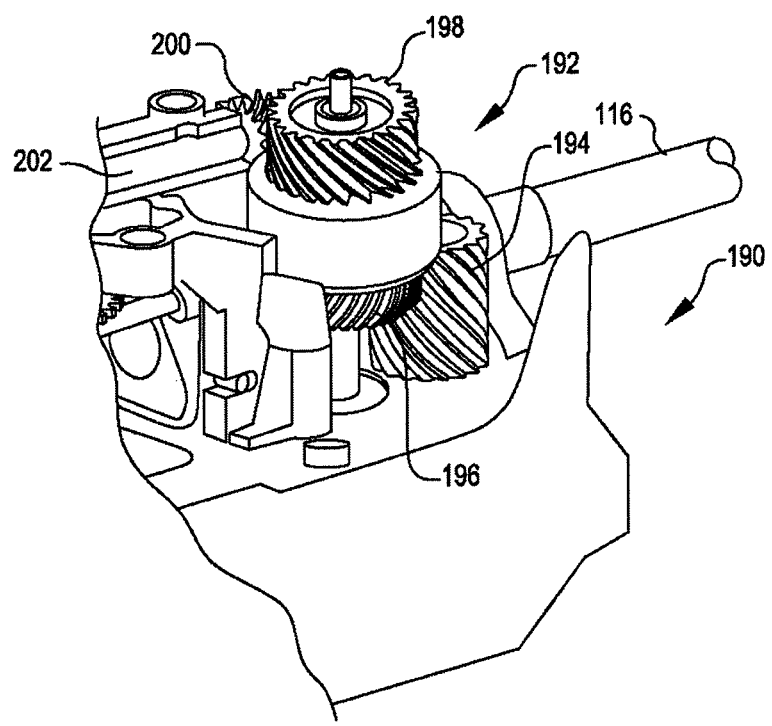
FIG. 13 is a perspective view illustrating a proximal chassis of a surgical instrument having a planetary gear box used to decouple instrument shaft roll and end effector actuation in a surgical instrument, in accordance with many embodiments.
Figure 14:
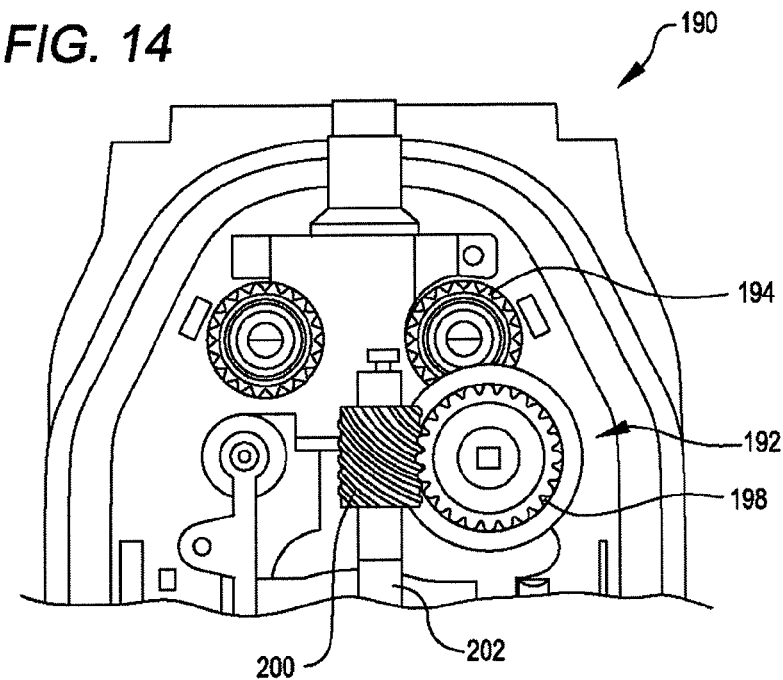
FIG. 14 is a plan view illustrating the proximal chassis of the surgical instrument of FIG. 13.
Figure 15:
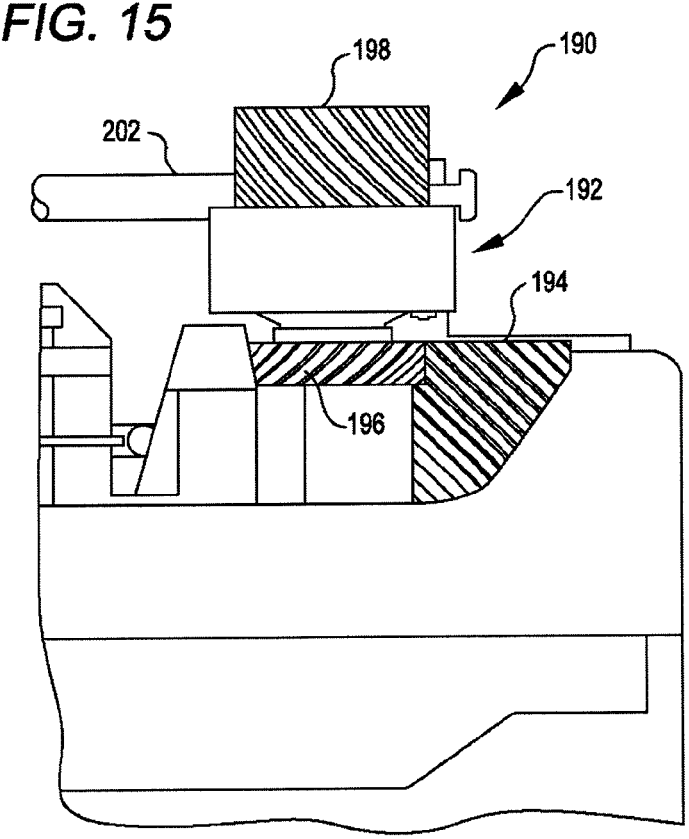
FIG. 15 is a side view illustrating the proximal chassis of the surgical instrument of FIG. 13.

FIG. 13 is a perspective view of a proximal chassis 190 of a robotic surgical instrument that includes a gear implemented differential 192, in accordance with many embodiments. The gear implemented differential 192 includes a planetary gear assembly having a sun gear, planet gears coupled to a carrier, and a ring gear. The carrier is rotationally coupled with an input coupler of the proximal chassis through an input shaft. The input shaft is aligned with the input coupler and is transverse to the instrument shaft. The sun gear is rotationally coupled with rotation of the instrument shaft 116 through helical gears 194, 196. Rotations of the carrier and the sun gear result in rotation of the ring gear. The ring gear is rotationally coupled with an end effector actuation mechanism through helical gears 198, 200, output shaft 202, and a drive shaft routed internal to the instrument shaft 116. FIG. 14 shows a plan view of the proximal chassis 190 and the gear implemented differential 192. And FIG. 15 shows a side view of the proximal chassis 190 and the gear implemented differential 192.

Figure 16:
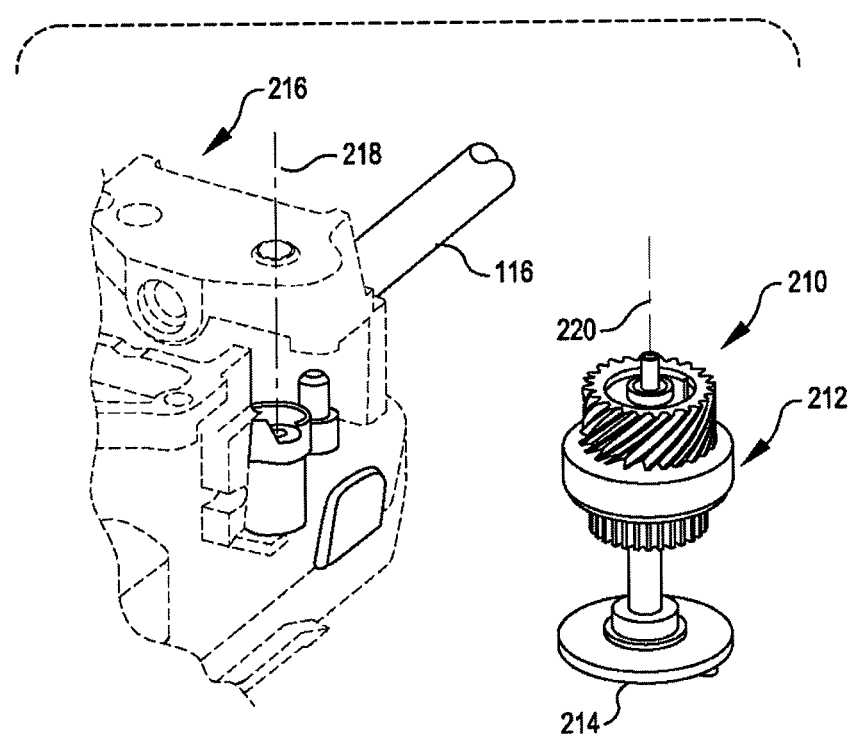
FIG. 16 is a partially exploded perspective view illustrating a planetary gear box coupled with an input coupler of a surgical instrument, in accordance with many embodiments.
Figure 17:
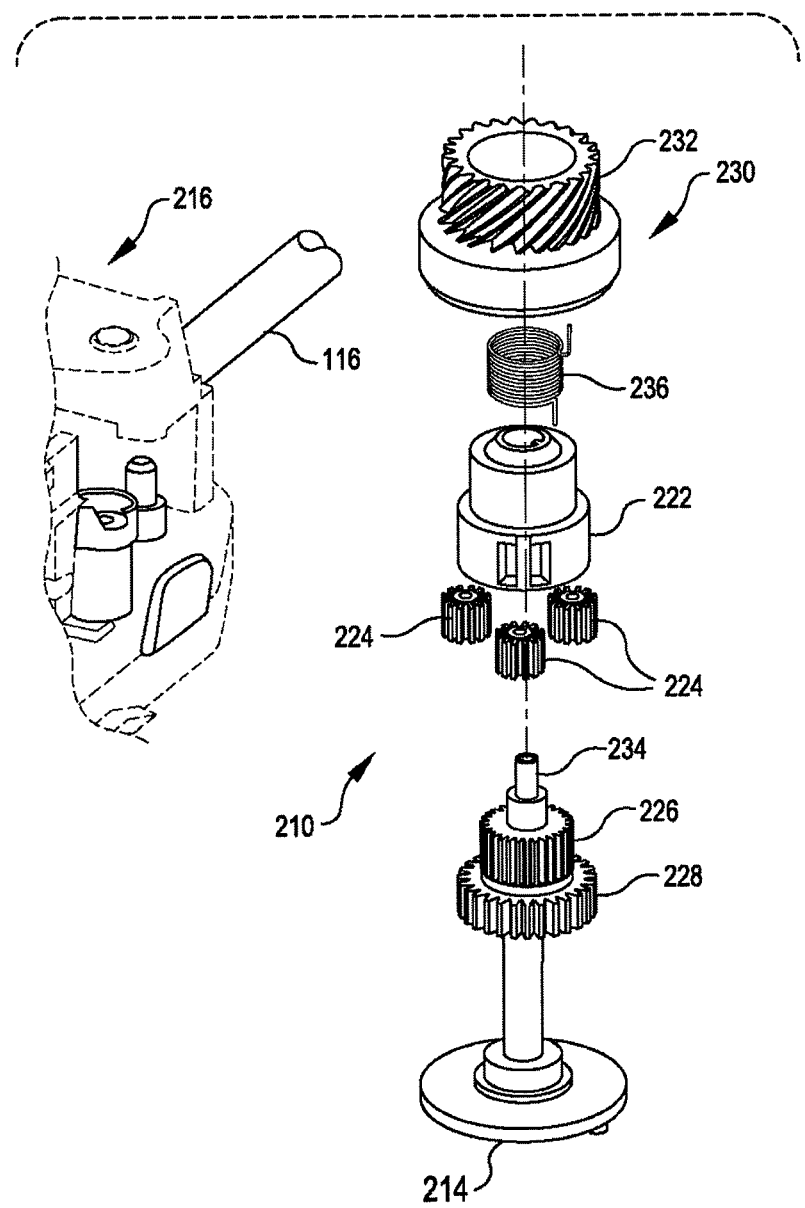
FIG. 17 is an exploded perspective view of the planetary gear box and input coupler of FIG. 16.

FIG. 16 and FIG. 17 are exploded views illustrating details of a gear implemented differential 210, in accordance with many embodiments. The gear implemented differential 210 includes a planetary gear box assembly 212. FIG. 16 shows the gear implemented differential 210 and attached input shaft and input coupler 214 displaced sideways from where they would be installed in a proximal chassis 216 of a robotic surgical instrument having an instrument shaft 116. An installed centerline 218 and a central axis 220 of the gear implemented differential 210 illustrate the offset from the installed position.

FIG. 17 is an exploded perspective view of the gear implemented differential 210, the input shaft, and the input coupler 214. The differential 210 includes a carrier 222 that is coupled with planet gears 224, a sun gear 226 that is rotationally driven by an input gear 228, a ring gear member 230 that has an internal ring gear and an external helical output gear 232. The carrier 222 is rotationally coupled with and driven by an input shaft 234, which is rotationally coupled with and driven by an input coupler 214. The input coupler 214 interfaces with and is rotationally driven by a corresponding output coupler of a robotic arm of a surgical robot when the proximal chassis 216 is mounted to the robotic arm. Rotation of the carrier 222 results in rotation of centerlines of the planet gears 224 around the central axis 220. The input gear 228 is rotationally coupled with rotation of the instrument shaft 116. The combined rotation of the sun gear 226 and the centerlines of planet gears 224 around the central axis 220 results in corresponding rotation of the ring gear member 230 about the central axis 220. The ring gear member 230 is drivingly coupled with an end effector actuation mechanism through the external helical output gear 232.

The gear implemented differential 210 includes a torsion spring 236 coupled between the carrier 222 and the proximal chassis 216. The torsion spring returns the carrier to a predetermined position following a disconnect between the carrier and an actuation source in the robotic arm, thereby returning the end effector actuation mechanism to a predetermined configuration.

In operation, the gear implemented differential 210 operates similar to the differential 118 discussed above. Additional gearing per known approaches can be used to account for directional and rotational speed differences between the instrument shaft 116 and the resulting output motion of the external helical output gear 232.

Example Planetary Gear Box Parameters

The following equation provides the relationship between rotations of the sun gear 226, the carrier 222, and the ring gear member 230.

$$(2+n)\omega_a + n\omega_S - 2(1+n)\omega_c = 0 \qquad \text{Equation (1)}$$

where: $n = N_s/N_p$ (form factor for the planetary gear box)
 $N_s$=number of sun gear teeth
 $N_p$=number of gear teeth on a planet gear
 $\omega_a$=angular velocity of the ring gear member (also known as "annulus")
 $\omega_s$=angular velocity of the sun gear
 $\omega_c$=angular velocity of the carrier As shown in equation (1), the angular velocity of the ring gear member 230 is a linear combination of the angular velocity of the sun gear 226 and the angular velocity of the carrier 222. Accordingly, in the gear implemented differential 210 (where the sun gear 226 is rotationally driven by rotation of the instrument shaft 116, where the carrier 222 is rotationally driven by the input coupler 214, and where the ring gear member 230 is rotationally coupled with an end effector actuation mechanism) rotation of the instrument shaft 116 results in a corresponding additional rotation of the ring gear member 230, thereby decoupling instrument shaft rotation from the actuation of the end effector actuation mechanism.

The following parameters provide an example configuration of a planetary gear box of a gear implemented differential 210.

$N_S = 24 \ N_p = 12 \ n = N_s/N_p = 2$ $N_a = N_s + 2N_p = 48$ number of ring gear teeth $DP = 64$ number of gear teeth/pitch diameter (teeth/inch)

$PD_s = N_s/DP = 0.375$ inches—pitch diameter of the sun gear $PD_p = N_p/DP = 0.1875$ inches—pitch diameter of a planet gear $PD_a = N_a/DP = 0.75$ inches—pitch diameter of the ring gear of the ring gear member For zero carrier angular velocity (corresponding to no rotational input through the input coupler 214), equation (1) reduces to:

$$(2+n)\omega_a + n\omega_s = 0 \qquad \text{Equation (1) with } \omega_c=0$$

For the above example planetary gear box parameters, n=2, which produces the following relationship between the angular velocity of the ring gear member ($\omega_a$) and the angular velocity of the sun gear ($\omega_s$):

$$\omega_a = -\frac{n}{(2+n)}\omega_s = -\frac{2}{(2+2)}\omega_s = -0.5\omega_s$$

To account for the difference in rotational direction between the sun gear 226 and the ring gear member 230 and to achieve an equal amount of rotation of a drive shaft rotationally coupled with an end effector actuation mechanism as that of the instrument shaft 116, additional gearing using known approaches can be used between the instrument shaft 116 and the sun gear 226 and/or between the ring gear member 230 and the drive shaft rotationally coupled with the end effector actuation mechanism.

Surgical Assembly Applications

The surgical assemblies disclosed herein can be employed in any suitable application. For example, the surgical assemblies disclosed herein can be employed in other surgical instruments, manual or powered, hand-held or robotic, directly controlled or teleoperated, for open or minimally invasive (single or multi-port) procedures. An example of such instruments include those with distal components that receive torque actuating inputs (e.g., for grip control functions, component orientation control functions, component position functions, etc.). Illustrative non-limiting examples include teleoperated or hand-held instruments that include stapling, cutting, tissue fusing, imaging device orientation and position control, high force grasping, biopsy, and end effector and orientation control.

Methods of Decoupling Instrument Shaft Roll and End Effector Actuation

Figure 18:
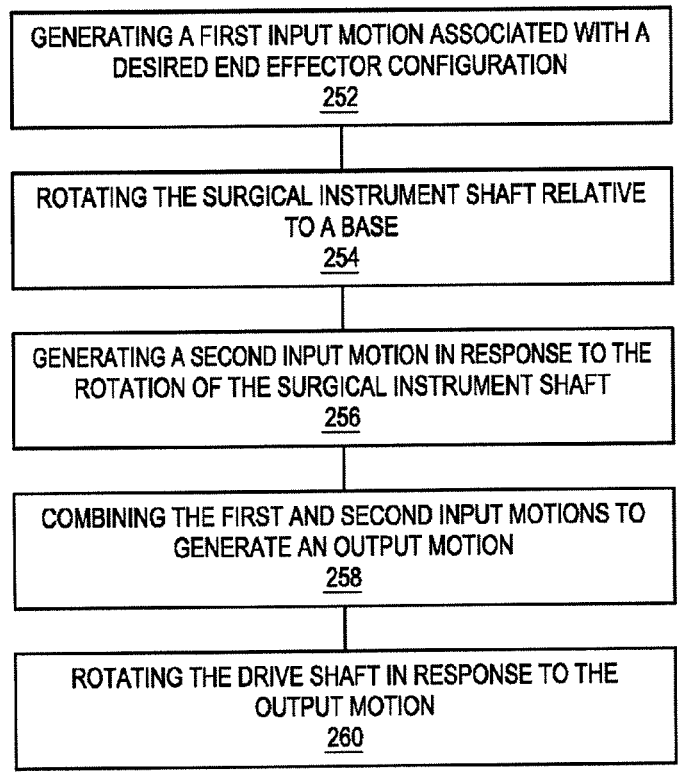
FIG. 18 illustrates acts of a method of decoupling rotation of a surgical instrument shaft from rotation of a drive shaft drivingly coupled with a mechanism of an end effector supported by the surgical instrument shaft, in accordance with many embodiments.

FIG. 18 illustrates acts of a method 250 of decoupling rotation of a surgical instrument shaft from rotation of a drive shaft drivingly coupled with a mechanism of an end effector supported by the surgical instrument shaft, in accordance with many embodiments. The method 250 can practiced, for example, by using any suitable differential, such as any of the differential 118, the cable implemented differential 130, the cable implemented differential 170, and the gear implemented differential 192 as described above. The method 250 includes generating a first input motion associated with a desired end effector configuration (act 252); rotating the surgical instrument shaft relative to a base, the surgical instrument shaft extending between a proximal end adjacent to the base and a distal end that supports the end effector (act 254); generating a second input motion in response to the rotation of the surgical instrument shaft relative to the base (act 256), combining the first and second input motions to generate an output motion (act 258), and rotating the drive shaft in response to the output motion (act 260). In many embodiments, the first and second input motions are combined such that no substantial rotation of the drive shaft relative to the surgical instrument occurs when the first input motion is zero.

Figure 19:
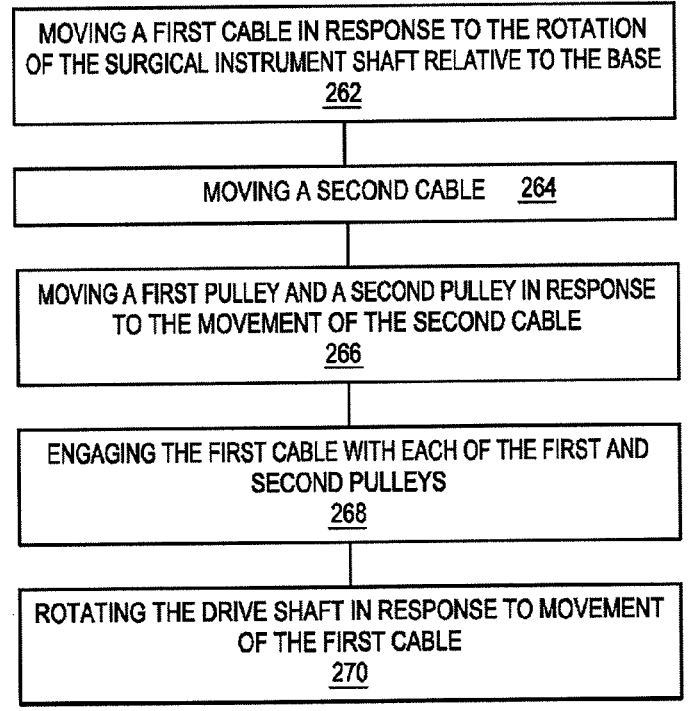
FIG. 19 illustrates acts relating to a cable driven differential that can be used in the implementation of the method of FIG. 18, in accordance with many embodiments.

FIG. 19 illustrates acts that can be used to practice the method 250 by using a cable implemented differential, such as any of those described herein. The acts include moving a first cable in response to the rotation of the surgical instrument shaft relative to the base (act 262), moving a second cable (act 264), moving a first pulley and a second pulley in response to the movement of the second cable (act 266), engaging the first cable with each of the first and second pulleys (act 268), and rotating the drive shaft in response to movement of the first cable (act 270). In many embodiments, the first cable is engaged with each of the first and second pulleys over an approximately 180 degree sector of the respective pulley.

Figure 20:
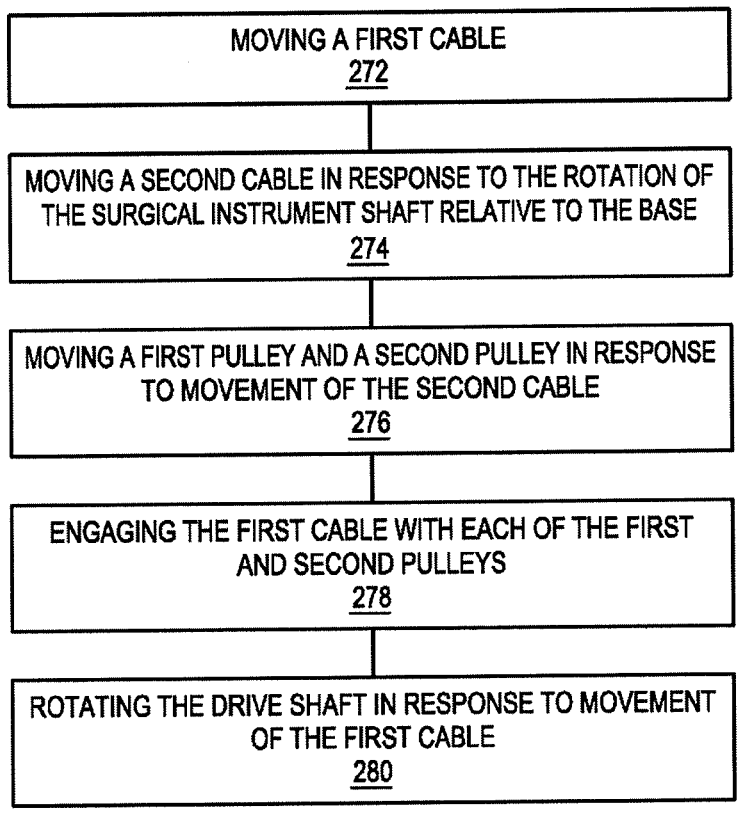
FIG. 20 illustrates acts relating to another cable driven differential that can be used in the implementation of the method of FIG. 18, in accordance with many embodiments.

FIG. 20 illustrates acts that can be used to practice the method 250 by using a cable implemented differential, such as any of those described herein. The acts include moving a first cable (act 272), moving a second cable in response to the rotation of the surgical instrument shaft relative to the base (act 274), moving a first pulley and a second pulley in response to the movement of the second cable (act 276), engaging the first cable with each of the first and second pulleys (act 278), and rotating the drive shaft in response to movement of the first cable (act 280). In many embodiments, the first cable is engaged with each of the first and second pulleys over an approximately 180 degree sector of the respective pulley.

Figure 21:
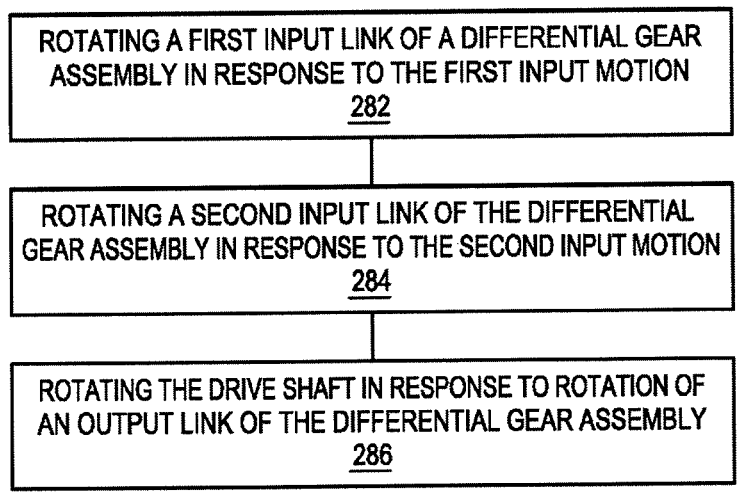
FIG. 21 illustrates acts relating to a differential gear assembly that can be used in the implementation of the method of FIG. 18, in accordance with many embodiments.

FIG. 21 illustrates acts that can be used to practice the method 250 by using a gear implemented differential, such as any of those described herein. The acts include rotating a first input link of a differential gear assembly in response to the first input motion (act 282), rotating a second input link of the differential gear assembly in response to the second input motion (act 284), and rotating the drive shaft in response to rotation of an output link of the differential gear assembly (act 286).

Method Applications

The methods disclosed herein can be employed in any suitable application. For example, the methods disclosed herein can be employed in surgical instruments, manual or powered, hand-held or robotic, directly controlled or teleoperated, for open or minimally invasive (single or multi-port) procedures. An example of such instruments include those with distal components that receive torque actuating inputs (e.g., for grip control functions, component orientation control functions, component position functions, etc.). Illustrative non-limiting examples include teleoperated or hand-held instruments that include stapling, cutting, tissue fusing, imaging device orientation and position control, high force grasping, biopsy, and end effector and orientation control.

Drive Shaft(s) Within a Rotatable Shaft

Figure 22:
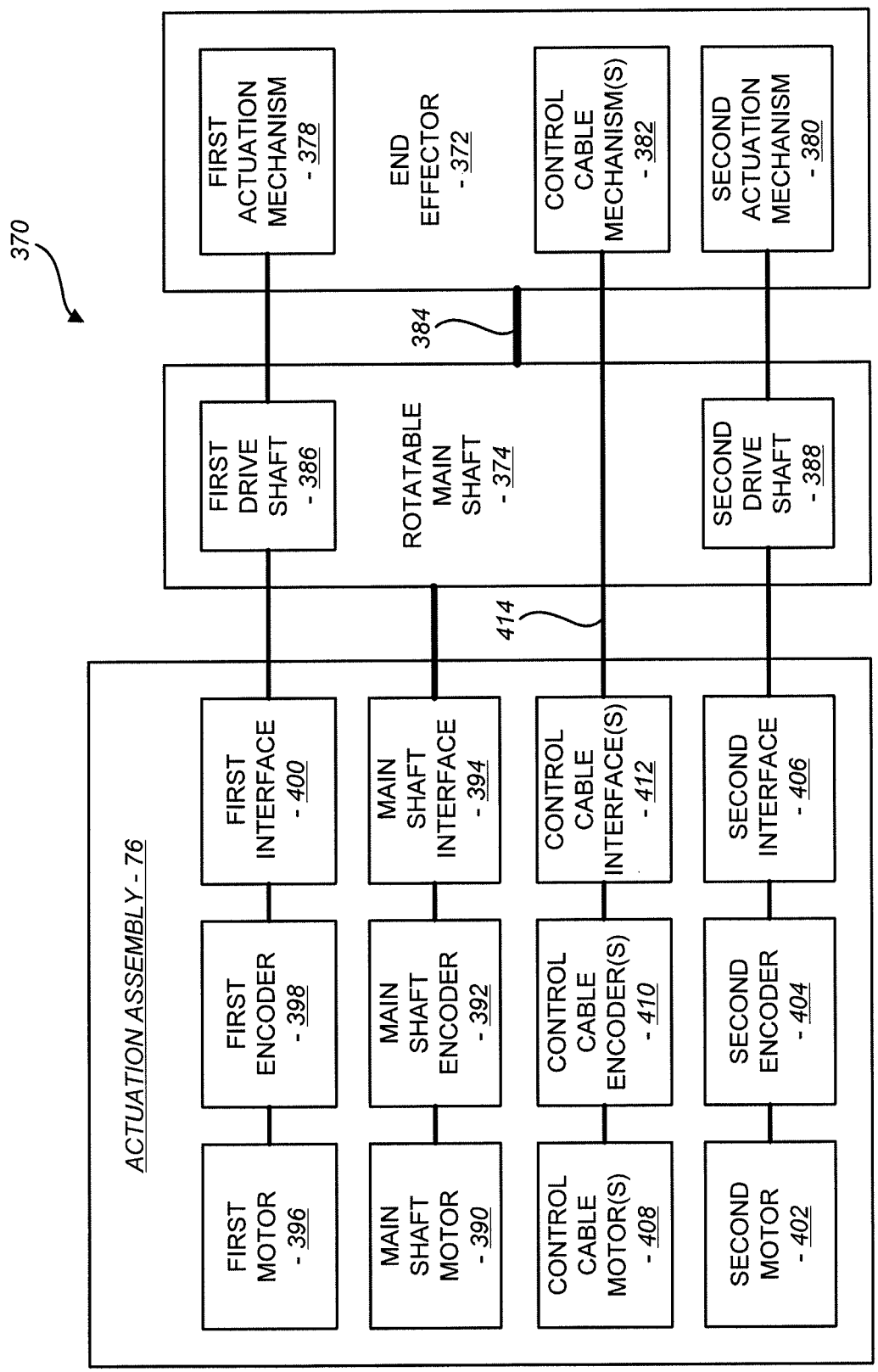
FIG. 22 diagrammatically illustrates a robotic assembly having two offset drive shafts within a rotatable main shaft, in accordance with many embodiments.

FIG. 22 diagrammatically illustrates a robotic assembly 370 having two offset drive shafts within a rotatable main shaft. The robotic assembly 370 includes an end effector 372 that is coupled with the distal end of a rotatable main shaft 374, and an actuation assembly 376 coupled with both the main shaft 374 and the end effector 372.

The end effector 372 includes an end effector base, a first actuation mechanism 378, a second actuation mechanism 380, and a control cable mechanism(s) 382. The end effector base is pivotally coupled to the rotatable main shaft 374. The first actuation mechanism 378 and the second actuation mechanism 380 are shaft driven and can be used to actuate and/or articulate a variety of end effector features and/or devices, for example, a clamping feature, a movable cutting feature, a cutting and stapling device, or another suitable end effector feature and/or device that can be actuated and/or articulated with a shaft driven mechanism. The control cable mechanism(s) 382 can also be used to actuate and/or articulate a variety of end effector features and/or devices, particularly those where a fast response is desired, for example, a grasping feature, a main shaft to end effector base wrist that is used to articulate the end effector base relative to the main shaft, or another suitable feature and/or device that can be actuated and/or articulated via one or more control cables.

The end effector base is coupled with the rotatable main shaft 374 so that a rotation of the main shaft 374 about a main shaft rotation axis produces a corresponding rotation of the end effector base. As discussed above, the ability to independently rotate the main shaft 374 provides increased end effector maneuverability relative to a non rotating main shaft, which may be beneficial during certain surgical procedures, for example, during certain minimally invasive surgical procedures. The end effector base can also be coupled with the rotatable main shaft 374 with a suitable wrist mechanism 384 that provides additional end effector maneuverability.

Two drive shafts are used to drive the end effector shaft driven actuation mechanisms. A first drive shaft 386 is mounted for rotation about a first drive shaft rotational axis that is offset from the main shaft rotation axis. The first drive shaft 386 is operatively coupled with the first actuation mechanism 378. Likewise, a second drive shaft 388 is mounted for rotation about a second drive shaft rotational axis that is offset from the main shaft rotation axis. The second drive shaft 388 is operatively coupled with the second actuation mechanism 380.

The actuation assembly 376 is coupled with the rotatable main shaft 374, the first drive shaft 386, the second drive shaft 388, and the control cable mechanism(s) 382. The rotatable main shaft 374 is mounted for rotation relative to a base of the actuation assembly 376. The actuation assembly 376 is operable to produce rotation of the rotatable main shaft 374 relative to the base. The actuation assembly 376 is also operable to generate any combination of rotation of the rotatable main shaft 374 relative to the base, rotation of the first drive shaft 386 relative to the rotatable main shaft 374, and rotation of the second drive shaft 388 relative to the rotatable main shaft 374. As such, the first actuation mechanism 378 and/or the second actuation mechanism 380 can be actuated independently and/or simultaneously with rotation of the rotatable main shaft 374.

The actuation assembly 376 is configured to provide the above described functionality in which the first drive shaft 386 and the second drive shaft 388 can be independently rotated relative to the rotatable main shaft 374, even during rotation of the rotatable main shaft 374 relative to the base. The actuation assembly 376 includes a main shaft motor 390 coupled with a main shaft encoder 392 and a main shaft interface 394, a first motor 396 coupled with a first encoder 398 and a first interface 400, a second motor 402 coupled with a second encoder 404 and a second interface 406, and a control cable motor(s) 408 coupled with a control cable encoder(s) 410 and a control cable interface(s) 412. The main shaft interface 394 is coupled with the rotatable main shaft 374 so as to transfer rotational motion from the main shaft motor 390 to the rotatable main shaft 374. The main shaft motor 390 can be fixedly coupled with the base so that the transferred rotational motion results in rotation of the rotatable main shaft 374 relative to the base. The main shaft encoder 392 measures the orientation of the main shaft motor 390, the main shaft interface 394, and/or the rotatable main shaft 374 and can be coupled with a controller (not shown in FIG. 22) so as to provide the controller with the measured orientation. The first interface 400 is coupled with the first drive shaft 386 so as to be operable to transfer rotational motion from the first motor 396 to the first drive shaft 386 during any orientation and/or rotational motion of the rotatable main shaft 374. The first encoder 398 measures the orientation of the first motor 396, the first interface 400, and/or the first drive shaft 386 and can be coupled with the controller so as to provide the controller with the measured orientation. The second interface 406 is coupled with the second drive shaft 388 so as to be operable to transfer rotational motion from the second motor 402 to the second drive shaft 388 during any orientation and/or rotational motion of the rotatable main shaft 374. The second encoder 404 measures the orientation of the second motor 402, the second interface 406, and/or the second drive shaft 388 and can be coupled with the controller so as to provide the controller with the measured orientation. The control cable interface(s) 412 is coupled with control cable(s) 414 that are operatively coupled with the control cable mechanism(s) 382. The control cable(s) 414 can be routed so as to tolerate a range of rotational orientations of the rotatable main shaft 374, for example, by being routed in the vicinity of the main shaft rotational axis to minimize changes in control cable length due to rotation of the rotatable main shaft 374, and by being configured to tolerate any twisting of control cable(s) and/or twisting between control cables that may result for some rotational orientations of the main shaft 374 (e.g., by having a construction that tolerates cable-to-cable rubbing). The control cable encoder(s) 410 measures the orientation of the control cable motor(s) 408 and/or the control cable interface(s) 412 and can be coupled with the controller so as to provide the controller with the measured orientation(s).

FIG. 23 is a simplified block diagram illustrating the integration of components of the robotic assembly 370 with a controller 416, in accordance with many embodiments. The controller 416 includes at least one processor 418, which communicates with a number of peripheral devices via a bus subsystem 420. These peripheral devices typically include a storage subsystem 422.

The storage subsystem 422 maintains the basic programming and data constructs that provide the functionality of the controller 416. Software modules for implementing the robotic assembly functionality discussed above are typically stored in the storage subsystem 422. The storage subsystem 422 typically includes a memory subsystem 424 and a file storage subsystem 426.

The memory subsystem 424 typically includes a number of memories including a main random access memory (RAM) 428 for storage of instructions and data during program execution and a read only memory (ROM) 430, in which fixed instructions are stored.

The file storage subsystem 426 provides persistent (non-volatile) storage for program and data files, and can include a hard drive, a disk drive, or other non-volatile memory such as a flash memory. An input device, for example a disk drive, can be used to input the software modules discussed above. Alternatively, other known structures may alternatively be used to input the software modules, for example, a USB port.

In this context, the term "bus subsystem" is used generically so as to include any mechanism for letting the various components and subsystems communicate with each other as intended. The bus subsystem 420 is shown schematically as a single bus, but a typical system has a number of buses such as a local bus and one or more expansion buses (e.g., ADB, SCSI, ISA, EISA, MCA, NuBus, or PCI), as well as serial and parallel ports.

The controller 416 controls components of the robotic assembly 370 in response to assorted received signals, including signals from the input control device(s) 36 (shown in FIG. 2), as well as from the main shaft encoder 392, the first encoder 398, the second encoder 404, and the control cable encoder(s) 410. The components controlled include the main shaft motor 390, the first motor 396, the second motor 402, and the control cable motor(s) 408. Additional components (not shown), such as digital/analog converters can be used to interface components with the controller 416.

FIG. 24 is a simplified block diagram illustrating the integration of a robotic surgery tool 432 within a robotic surgery system, in accordance with many embodiments. The tool 432 includes a proximal tool chassis 434 configured to be releasably mountable on a manipulator 436 having a tool interface configured to interface with the proximal tool chassis 434. The tool 432 further includes an elongate main shaft 374 that is mounted to rotate relative to the proximal tool chassis 434 when rotated by a main shaft motor, as discussed above. An end effector 440 is coupled with a distal end of the main shaft 374 so as to rotate along with the main shaft. A main control system 442 is operatively coupled with the manipulator 436. An auxiliary control system 444 can also be operatively coupled with the manipulator 436. The combination of the main control system 442 and the auxiliary control system 444 can be used to control all possible articulations of the tool 432 via the manipulator 436. For example, the auxiliary control system 444 can control the drive motors for first drive shaft rotation and second drive shaft rotation. The main control system 442 can control a drive motor for main shaft rotation and one or more control cable drive motors. Such an auxiliary controller can be used to supplement existing robotic surgery system configurations so as to allow the use of the presently disclosed robotic tools having one or more offset drive shafts routed within an independently rotating main shaft.

Figure 25:
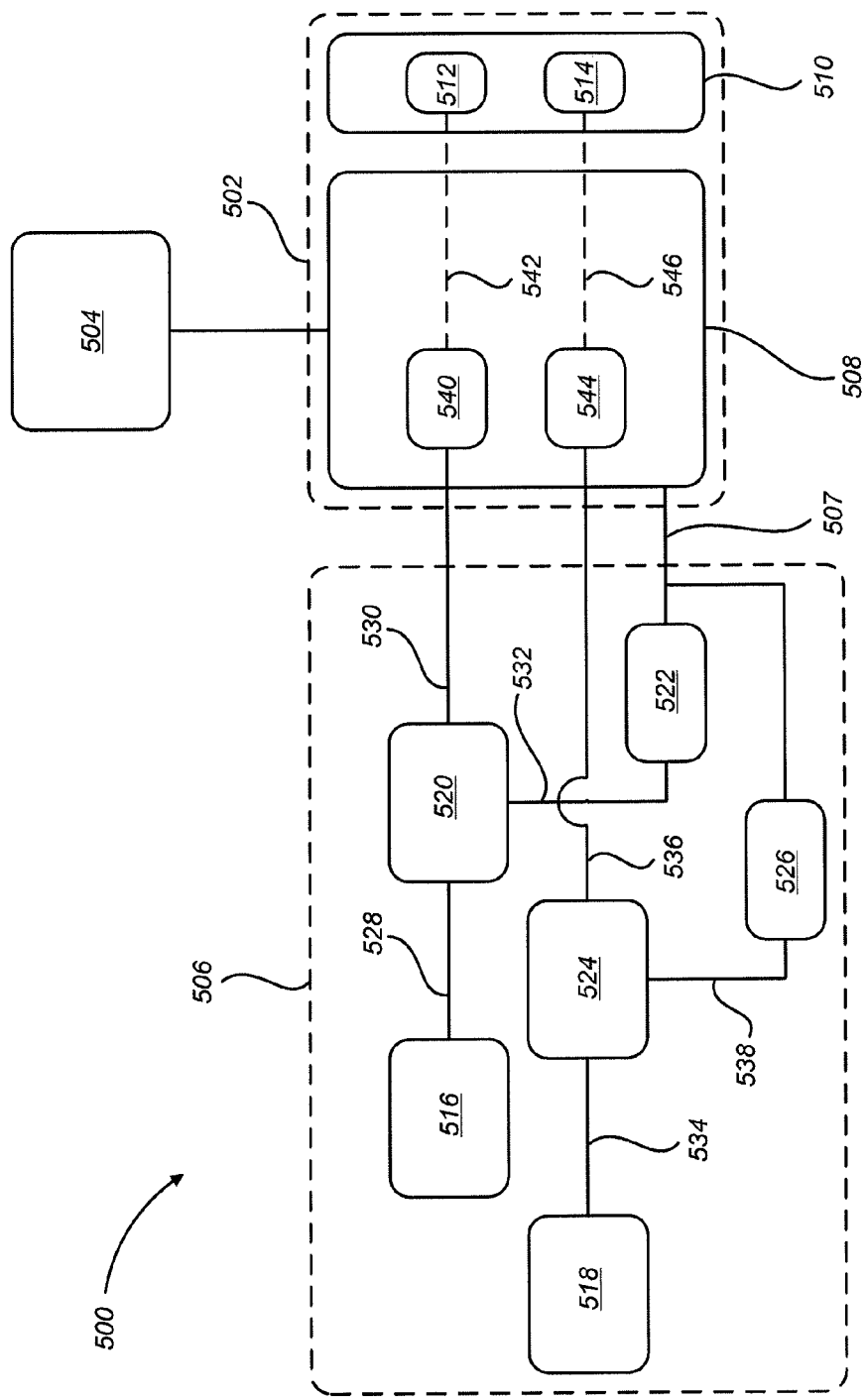
FIG. 25 diagrammatically illustrates a surgical assembly in which drive motors are coupled with an end effector and a main shaft that supports the end effector so as to avoid unintended rotation of the main shaft, in accordance with many embodiments.

Coupling a Drive Motor(s) to an End Effector and a Main Shaft Supporting the End Effector so as to Avoid Unintended Rotation of the Main Shaft FIG. 25 diagrammatically illustrates a surgical assembly 500, in accordance with many embodiments, in which drive motors used to actuate end effector rotary mechanisms are coupled with a main shaft/end effector assembly so as to avoid unintentional rotation of the main shaft/end effector assembly during actuation of the end effector rotary mechanisms. The surgical assembly 500 includes a main shaft/end effector assembly 502 that is rotationally mounted to a base (e.g., manipulator 436 as illustrated in FIG. 24), a main shaft drive 504 that rotationally drives the main shaft/end effector assembly 502 relative to the base, and a counteracting actuation assembly 506 that is rotationally coupled with the main shaft/end effector assembly 502 so as to provide actuation torques to the end effector rotary mechanisms and a counteracting torque 507 to the main shaft/end effector assembly 502.

The main shaft/end effector assembly 502 includes a main shaft 508 that is rotationally mounted to the base and rotationally driven by the main shaft drive 504, and an end effector 510 that is supported by the main shaft 508. The end effector 510 includes a first rotary mechanism 512 and a second rotary mechanism 514. The first and second rotary mechanisms 512, 514 can be used to articulate end effector components, for example, a clamping jaw, a stapling device, a cutting device, and the like.

Because of dimensional constraints imposed on minimally invasive surgical tools, it is desirable to provide actuation torques to the first and second rotary mechanisms 512, 514 from a source external to the main shaft/end effector assembly 502. In such a configuration, however, because the first and second rotary mechanisms 512, 514 are part of the end effector 510, which is supported by the main shaft 508 of the main shaft/end effector assembly 502, when actuation torques are transmitted to the first and second rotary mechanisms 512, 514 from the external source some or all of the transmitted actuation torque may be reacted by the main shaft 508. The actuation torque reacted by the main shaft/end effector assembly 502 is also reacted by the main shaft drive 504. As a result, the main shaft drive 504 may be back-drivable via a torque of sufficient magnitude reacted by the main shaft/end effector assembly 502. In other words, the main shaft drive 504 may have a back-driving torque threshold such that the main shaft/end effector assembly 502 back drives the main shaft drive when the main shaft/end effector assembly 502 is subject to a net torque (including any torque necessary to overcome friction induced restraint) over the back-driving torque threshold and does not back drive the main shaft drive when the main shaft/end effector assembly 502 is subject to a net torque under the back-driving torque threshold. And it may also be desirable to avoid the use of certain mechanisms that prevent rotational driving (also known as back driving) of the main shaft drive 504 by the main shaft 508, for example, mechanisms such as torque brakes, irreversible gearing, and the like, so as to avoid the related cost, size, weight, associated detrimental characteristics, and/or expense.

In the surgical assembly 500, the counteracting actuation assembly 506 is the external source that generates the actuation torques that are transmitted to the first and second rotary mechanisms 512, 514. The counteracting actuation assembly 506 also generates a balancing torque that is transmitted to the main shaft 508 so as to prevent back driving of the main shaft drive 504. The counteracting actuation assembly 506 includes a first drive motor 516, a second drive motor 518, a first transmission 520, a first rotational coupling 522, a second transmission 524, and a second rotational coupling 526.

The first drive motor 516 is rotationally coupled with the first rotary mechanism 512 and the main shaft 508 via the first transmission 520 and the first rotational coupling 522. The first drive motor 516 is rotationally coupled with a first input link 528 of the first transmission and transmits a first input torque to the first input link 528. The first transmission 520 provides a first gear ratio between the first input link 528 and a first output link 530 of the first transmission 520. The first output link 530 is rotationally coupled with the first rotary mechanism 512. The first rotational coupling 522 is connected between a first base link 532 of the first transmission 520 and the main shaft 508. The first rotational coupling 522 provides a second gear ratio between the first base link 532 and the main shaft 508. The first base link 532 is not rotationally grounded (e.g., not rotationally grounded to the base to which the main shaft 508 is rotationally mounted).

The first gear ratio provided by the first transmission 520 is sufficiently greater than one so that the first output link 530 transmits a torque that exceeds the first input torque. Because the first base link 532 of the first transmission 520 is not rotationally grounded, the difference between the torque transmitted by the first output link 530 and the first input torque is balanced by a torque in the opposite direction that is transmitted from the first base link 532 to the first rotational coupling 522. In many embodiments, the first gear ratio is significantly greater than one so that the torque transmitted by the first output link 530 and the torque in the opposite direction that is transmitted from the first base link 532 to the first rotational coupling 522 have roughly equivalent magnitudes. For example, in an embodiment where the first gear ratio is 9 to 1, the torque transmitted by the first output link 530 is 9 times the first input torque. And the torque in the opposite direction transmitted by the first base link 532 to the first rotational coupling 522 has a magnitude that is 8 times the magnitude of the first input torque.

The second gear ratio provided by the first rotational coupling 522 is selected so that the torque transmitted to the main shaft 508 by the first rotational coupling 522 sufficiently balances the torque transmitted into the main shaft/end effector assembly 502 by the first output link 530 so as to inhibit rotational driving of the main shaft drive 504 by the main shaft/end effector assembly 502. Where the main shaft drive 504 has a non-zero back-driving torque threshold, the second gear ratio can be selected from a range of gear ratios and still result in the inhibition of rotational driving of the main shaft drive by the main shaft/end effector assembly 502. Ideally, the second gear ratio is selected such that the torque transmitted to the main shaft by the first rotation coupling substantially balances the torque transmitted into the main shaft/end effector assembly 502 by the first output link 530. And although not illustrated in FIG. 9, the first output link 530 of the first transmission 520 need not be directly rotationally coupled to the main shaft/end effector assembly 502, but instead can be coupled in a way so as to provide a non-unity gear ratio between the first output link 530 and the main shaft/end effector assembly 502. Where such a non-unity gear ratio exists, the second gear ratio provided by the first rotational coupling 522 can be configured to account for the additional non-unity gear ratio.

In a similar fashion, the second drive motor 518 is rotationally coupled with the second rotary mechanism 514 and the main shaft 508 via the second transmission 524 and the second rotational coupling 526. The second drive motor 518 is rotationally coupled with a second input link 534 of the second transmission and transmits a second input torque to the second input link 534. The second transmission 524 provides a third gear ratio between the second input link 534 and a second output link 536 of the second transmission 524. The second output link 536 is rotationally coupled with the second rotary mechanism 514. The second rotational coupling 526 is connected between a second base link 538 of the second transmission 524 and the main shaft 508. The second rotational coupling 526 provides a fourth gear ratio between the second base link 538 and the main shaft 508. The second base link 538 is not rotationally grounded (e.g., not rotationally grounded to the base to which the main shaft 508 is rotationally mounted).

The third gear ratio provided by the second transmission 524 is sufficiently greater than one so that the second output link 536 transmits a torque that exceeds the second input torque. Because the second base link 538 of the second transmission 524 is not rotationally grounded, the difference between the torque transmitted by the second output link 536 and the second input torque is balanced by a torque in the opposite direction that is transmitted from the second base link 538 to the second rotational coupling 526. In many embodiments, the third gear ratio is significantly greater than one so that the torque transmitted by the second output link 536 and the torque in the opposite direction that is transmitted from the second base link 538 to the second rotational coupling 526 have roughly equivalent magnitudes. For example, in an embodiment where the third gear ratio is 9 to 1, the torque transmitted by the second output link 536 is 9 times the second input torque. And the torque in the opposite direction transmitted by the second base link 538 to the second rotational coupling 526 has a magnitude that is 8 times the magnitude of the second input torque.

The fourth gear ratio provided by the second rotational coupling 526 is selected so that the torque transmitted to the main shaft 508 by the second rotational coupling 526 sufficiently balances the torque transmitted into the main shaft/end effector assembly 502 by the second output link 536 so as to inhibit rotational driving of the main shaft drive 504 by the main shaft/end effector assembly 502. Where the main shaft drive 504 has a non-zero back-driving torque threshold, the fourth gear ratio can be selected from a range of gear ratios and still result in the inhibition of rotational driving of the main shaft drive by the main shaft/end effector assembly 502. Ideally, the fourth gear ratio is selected such that the torque transmitted to the main shaft by the second rotation coupling substantially balances the torque transmitted into the main shaft/end effector assembly 502 by the second output link 536. And although not illustrated in FIG. 25, the second output link 536 of the second transmission 524 need not be directly rotationally coupled to the main shaft/end effector assembly 502, but instead can be coupled in a way so as to provide a non-unity gear ratio between the second output link 536 and the main shaft/end effector assembly 502. Where such a non-unity gear ratio exists, the fourth gear ratio provided by the second rotational coupling 524 can be configured to account for the additional non-unity gear ratio.

While the first and second output links 530, 536 can be directly rotationally coupled with the first and second rotary mechanisms 512, 514, respectively, the main shaft/end effector assembly 502 includes a first gear assembly 540 that provides a gear ratio between the first output link 530 and a first drive shaft 542 that is rotationally coupled with the first rotary mechanism 512 and a second gear assembly 544 that provides a gear ratio between the second output link 536 and a second drive shaft 546 that is rotationally coupled with the second rotary mechanism 514. For both the first and second gear assemblies 540, 544, the torque differential between their inputs and outputs are reacted into the main shaft 508. Regardless of the gear ratios provided by the first and second gear assemblies 540, 544, because the first and second gear assemblies 540, 544 are part of the main shaft/end effector assembly 502 any torque differentials generated by non-unity gear ratios of the first and second gear assemblies 540, 544 are reacted by the main shaft 508 as are the torques transmitted to the first and second rotary mechanisms 512, 514. As a result, the gear ratios of the first and second gear assemblies 540, 544 do not impact the configuration (e.g., gear ratios) of the counteracting actuation assembly 506 with respect to the magnitude of the counteracting torque 507 used to counteract the actuation torques transmitted to the main shaft/end effector assembly 502 by the first and second output links 530, 536.

The torque(s) transmitted into the main shaft/end effector assembly 502 via the first and second output links 530, 536 can exceed the back-driving torque threshold of the main shaft drive 504 while counteracting torque transmitted to the main shaft 508 via the counteracting actuation assembly 506 inhibits rotational driving of the main shaft drive 504. The counteracting actuation assembly 506 is configured such that the magnitude of the counteracting torque differs from the magnitude of the torque(s) transmitted into the main shaft/end effector assembly 502 by the first and second output links 530, 536 by a net torque magnitude that is less than the back-driving torque threshold for the main shaft drive 504 even when the torque transmitted into the main shaft/end effector assembly 502 by the first and second output links 530, 536 exceeds the back-driving torque threshold. Preferably, the net torque magnitude is less than 50 percent of the back-driving torque threshold, even when the torque transmitted into the main shaft/end effector assembly 502 by the first and second output links 530, 536 exceeds the back-driving torque threshold. More preferably, the net torque magnitude is less than 25 percent of the back-driving torque threshold, even when the torque transmitted into the main shaft/end effector assembly 502 by the first and second output links 530, 536 exceeds the back-driving torque threshold. More preferably still, the net torque magnitude is less than 10 percent of the back-driving torque threshold, even when the torque transmitted into the main shaft/end effector assembly 502 by the first and second output links 530, 536 exceeds the back-driving torque threshold. And ideally, the net torque magnitude is less than 2 percent of the back-driving torque threshold, even when the torque transmitted into the main shaft/end effector assembly 502 by the first and second output links 530, 536 exceeds the back-driving torque threshold. For example, in a scenario where the main shaft/end effector assembly 502 is not rotationally coupled with the main shaft drive 504 (e.g., in a failure scenario or where the coupling between the surgical assembly 500 and the surgical robot has not been properly established), friction in the surgical assembly 500 that acts in restraint to rotation of the main shaft/end effector assembly 502 relative to the base may be sufficient to prevent rotation of the main shaft/end effector assembly 502 where the net torque magnitude is less than 2 percent of the back-driving torque threshold.

The first rotational coupling 522 and the second rotational coupling 536 can share one or more common components that are rotationally coupled with the main shaft 508. For example, a common drive shaft can be rotationally coupled with the main shaft 508 to transmit counteracting torque from one or both of the base links 532, 538 to the main shaft 508.

Figure 26:
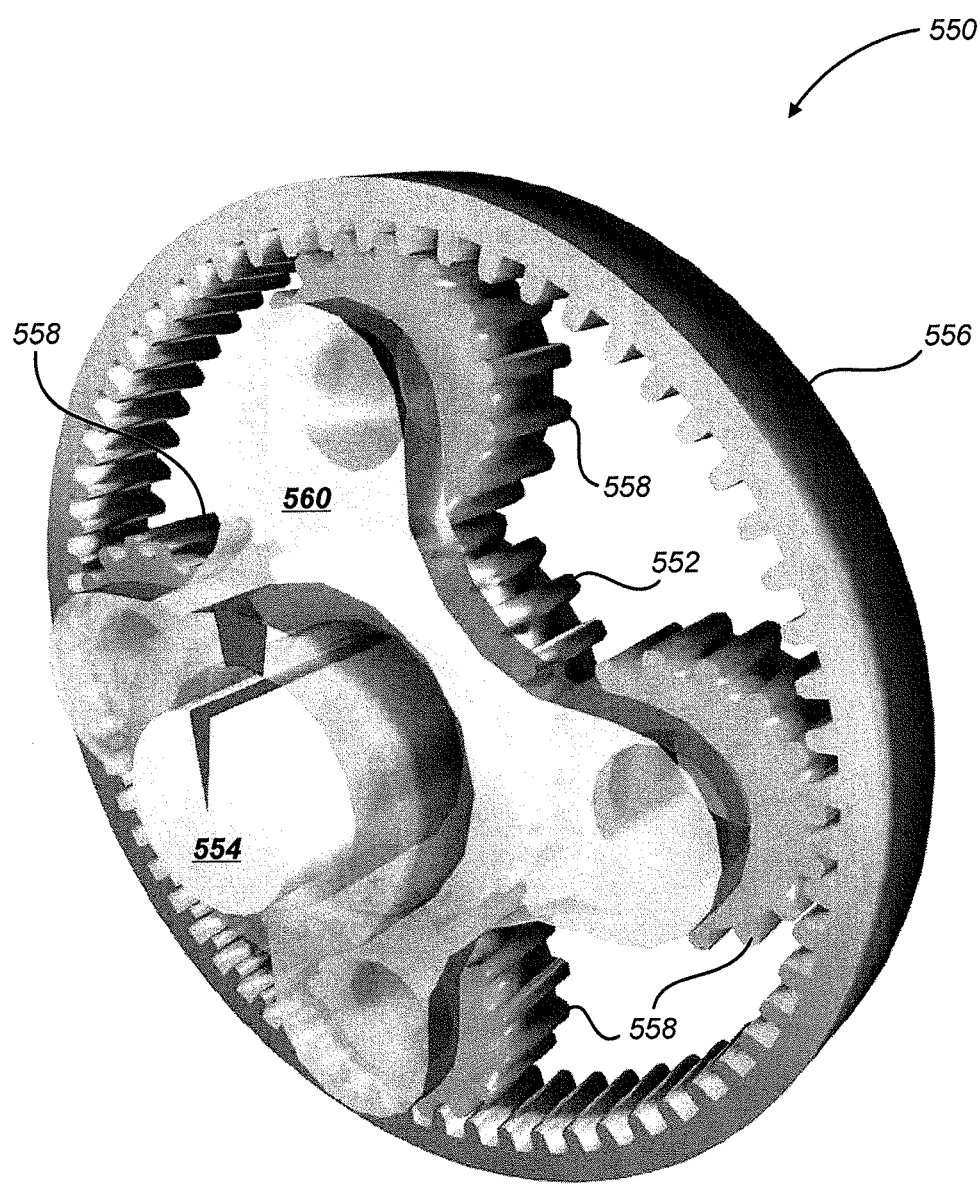
FIG. 26 is a perspective view of a planetary gear assembly, in accordance with many embodiments.

While any suitable type of transmission(s) can be used for the first and second transmissions, a planetary gear box can be used and can be configured to provide a suitable gear ratio. Such a planetary gear box can be configured to have a suitably small size to allow use in the counteracting actuation assembly 506. FIG. 26 illustrates an exemplary planetary gear set 550. The planetary gear set 550 includes a sun gear 552 that is attached to an input link 554, a ring gear 556, four planet gears 558 distributed around the sun gear 552 and rotationally coupling the sun gear 552 to the ring gear 556, and a carrier 560 that is rotationally coupled with and supports each of the planet gears 558.

Moreover, planetary gear boxes provide suitable features that can be used, in any possible combination, as the first and second input links 528, 534, the first and second output links 530, 536, and the first and second base links 532, 538 of the first and second transmissions 520, 524. For example, a sun gear can correspond to any one of the first and second input links, the first and second output links, and the first and second base links. Likewise, a carrier can correspond to any one of the first and second input links, the first and second output links, and the first and second base links. And a ring gear can correspond to any one of the first and second input links, the first and second output links, and the first and second base links. As a specific example of a suitable combination, a sun gear can correspond to the first/second input link, a carrier can correspond to the first/second output link, and a ring gear can correspond to the first/second base link. As another example, a sun gear can correspond to the first/second output link, a carrier can correspond to the first/second input link, and a ring gear can correspond to the first/second base link. And for the purposes of further illustration, a carrier or a sun gear can correspond to the first/second base link.

FIG. 27a, through FIG. 29c illustrate an embodiment of a minimally invasive robotic surgical instrument assembly 600 in accordance with the surgical assembly 500 of FIG. 9. Accordingly, the above discussion regarding the surgical assembly 500 applies to the surgical instrument assembly 600 and therefore portions of the above discussion may be omitted here. The instrument assembly 600 includes an actuation assembly 602 disposed at a proximal end of the instrument assembly. A main shaft 604 is rotationally mounted to the actuation assembly 602. A first drive shaft 606 and a second drive shaft 608 are mounted for rotation within the main shaft 604, and transmit torque to a first rotary mechanism and a second rotary mechanism, respectively, of an end effector (not shown) supported at a distal end of the instrument assembly. FIG. 11a is a perspective exterior view of the actuation assembly. FIG. 11b is an exploded perspective view of the instrument assembly 600 that shows a motor pack 610 decoupled from drive couplings 612 through which the first and second drive motors are rotationally coupled with the main shaft 604 and the first and second drive shafts 606, 608.

Figures 28A, 28B:
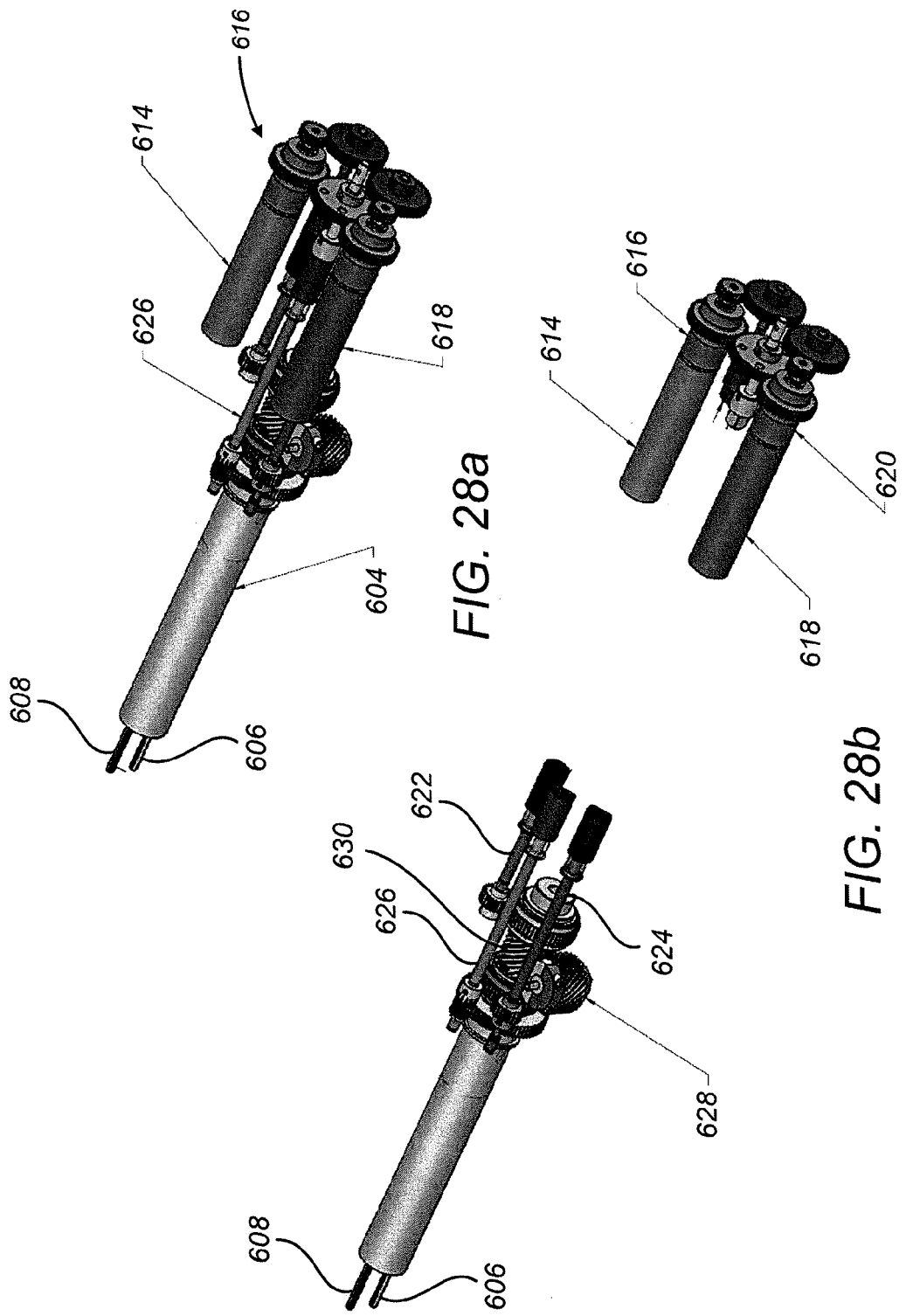
FIG. 28a is a perspective view of internal components of the instrument assembly of FIG. 27a illustrating the drive motors and components used to rotationally couple the drive motors to the main shaft and the respective internal drive shafts.
FIG. 28b is an exploded perspective view illustrating the internal components of FIG. 28a in a decoupled state corresponding to FIG. 28b.

FIG. 28a is a perspective view of internal components of the instrument assembly 600. And FIG. 28b is an exploded perspective view illustrating the internal components of FIG. 28a in a decoupled state corresponding to FIG. 27b. FIG. 29a is a perspective view of the internal components of the instrument assembly 600 with a second drive motor, a second planetary gear transmission, and a second coupling shaft removed so as to not obscure the illustration of the remaining components. FIG. 29b is an end view of the internal components of FIG. 29a. And FIG. 29c illustrates cross section A-A of FIG. 29b. The instrument assembly 600 includes a first drive motor 614, a first planetary transmission 616, a second drive motor 618, a second planetary transmission 620, a first coupling shaft 622, a second coupling shaft 624, and a common feedback shaft 626. Because the first and second planetary gear transmissions 616, 618 are rotationally grounded to the main shaft 604, the first and second planetary gear transmissions 616, 618 rotate relative to the first and second drive motors 614, 618, respectively, in response to rotation of the main shaft 604.

The first coupling shaft 622 forms part of a torque path between the carrier of the first planetary transmission 616 and the first drive shaft 606. The first drive motor 614 transmits a first input torque to a sun gear of the first planetary transmission 616. A carrier of the first planetary transmission 616 is rotationally coupled with the first coupling shaft 622 via intermeshing pinion gears. And the first coupling shaft 622 is rotationally coupled with the first drive shaft 606 via a pair of pinion gears and a ring gear as illustrated in FIG. 29a and FIG. 29c as well as described in U.S. Provisional Application No. 61/260,919, entitled "MOTOR INTERFACE FOR PARALLEL DRIVE SHAFTS WITHIN AN INDEPENDENTLY ROTATING MEMBER," filed Nov. 13, 2009, (Attorney Docket No. ISRG02360PROV), the full disclosure of which is hereby incorporated herein by reference.

Likewise, the second coupling shaft 624 forms part of a torque path between the carrier of the second planetary transmission 620 and the second drive shaft 608. The second drive motor 618 transmits a second input torque to a sun gear of the second planetary transmission 620. A carrier of the second planetary transmission 620 is rotationally coupled with the second coupling shaft 624 via intermeshing pinion gears. And the second coupling shaft 624 is rotationally coupled with the second drive shaft 608 via a pair of pinion gears and a ring gear as described in U.S. Provisional Application No. 61/260,919, entitled "MOTOR INTERFACE FOR PARALLEL DRIVE SHAFTS WITHIN AN INDEPENDENTLY ROTATING MEMBER," filed Nov. 13, 2009, incorporated by reference above.

The common feedback shaft 626 forms part of a torque path between the base link of the first planetary transmission 616 and the main shaft 604, as well as part of a torque path between the base link of the second planetary transmission 620 and the main shaft. The base link for the first planetary transmission 616 is rotationally coupled with the common feedback shaft 626 via a pair of pinion gears, one of which forms part of the base link of the first planetary transmission 616. Likewise, the base link of the second planetary transmission 620 is rotationally coupled with the common feedback shaft 626 via a pair of pinion gears, one of which forms part of the base link of the second planetary transmission 620. The common feedback shaft 626 is rotationally coupled with the main shaft 604 via a pair of pinion gears, one of which is directly rotationally coupled with the main shaft. The main shaft 604 is rotationally coupled with a main drive motor (not shown) via a pair of helical gears 628, 630.

In operation, when the main shaft is not being rotated, the common feedback shaft 626 and the base links of the first and second transmissions are also not rotating due to being rotationally coupled with the main shaft. Because the base links of the first and second planetary transmissions are not rotationally grounded to the base of the actuation assembly, the base links are free to rotationally deflect as required to transmit counteracting torque to the main shaft in response to input torques from the drive motors, and the base links are free to rotate as dictated by the rotation of the common drive shaft as dictated by any rotation of the main shaft by the main drive motor.

The instrument assembly 600 provides numerous advantages relative to alternate approaches that were evaluated to prevent undesirable main shaft rotation due to the transmission of actuation torque to rotary mechanisms of an end effector. For example, the instrument assembly 600 provides for the transmission of high levels of torque to one or both of the first and second rotary mechanisms of an end effector that is supported by an independently rotatable main shaft while at the same time providing for the transmission of counteracting torque to the main shaft, which can thereby result in substantially no net torque being applied to the main shaft that might back drive a main drive motor used to rotate the main shaft. The transmission of the counteracting torque is accomplished passively, thereby avoiding the use of components that would be necessary with an active approach. The instrument assembly 600 provides continuously linear performance in both rotational directions with no possibility for sudden release of energy. The instrument assembly 600 is compatible with realistic packing solutions considering the relatively large size of the motors and the gearboxes relative to the size of the main shaft. The instrument assembly 600 also requires no additional power to be applied relative to comparable instrument assemblies. The instrument assembly 600 also exhibits substantial invariance to friction, wear, backlash, manufacturing precision, and the stiffness of components used in the mechanism. Because the gearing creates a kinematically closed system between the transmissions and the main shaft, any backlash is taken up in that closed system and thus no net torque above the mechanism's calculated residual torque is ever applied to the main shaft/end effector assembly. And all of the foregoing advantages are provided in an instrument assembly that provides for free rotation of the main shaft by the main drive motor during the transmission of torque to one or both of the first and second rotary mechanisms of the end effector.

The alternate approaches evaluated failed to provide one or more of the foregoing advantages. The alternate approaches evaluated included unidirectional spur gears, non-back drivable worm gear, friction brake, main shaft rotational lock, extra power applied via the main drive motor, active compensation of main shaft rotation via the main drive motor, using an auxiliary motor to compensate for the exerted torque, and mounting the motors and gear boxes to the main shaft. Self locking gear concepts, in particular, suffer from a problem wherein a change in the direction of rotation while under load can cause a sudden and rapid release of mechanical energy as the gear set goes from locked to unlocked. A brake has a similar defect in that release of the brake can suddenly release energy.

Torque Balance Calculations for Example Gear Ratios

Figure 30:
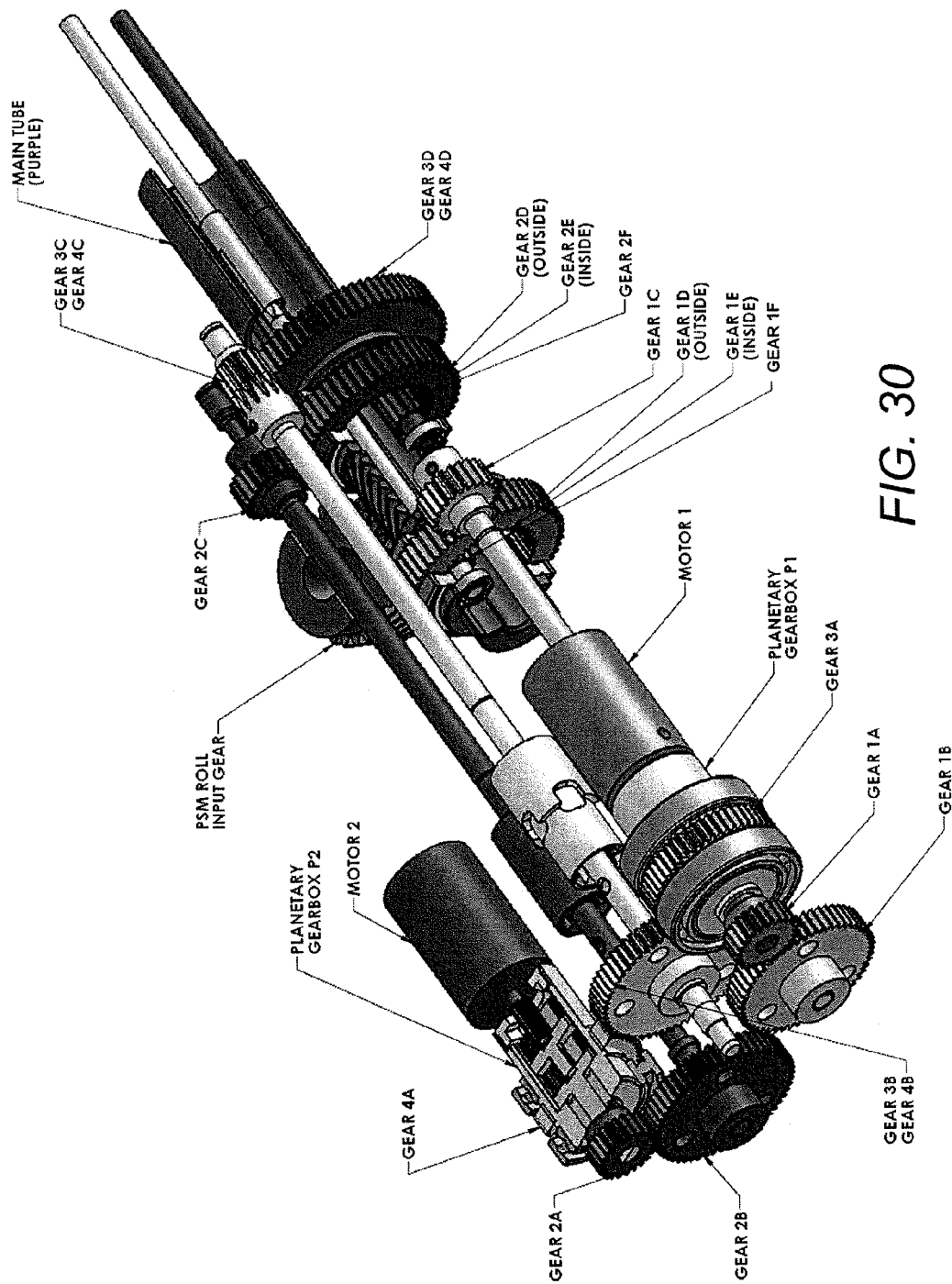
FIG. 30 is a perspective view of internal components of the instrument assembly of FIG. 27a illustrating the drive motors, gear boxes, and gears used to rotationally couple the drive motors to the respective internal drive shafts and the main shaft.

FIG. 30 provides reference identifications for the following discussion regarding exemplary gear ratios that can be used in the surgical assembly 500 discussed above. Because the counteracting actuation assembly 506 uses a similar configuration for coupling the first and second drive motors 516, 518 with the main shaft/end effector assembly 502, the following discussion with be presented with respect to coupling the first drive motor 516 with the main shaft/end effector assembly 502 with the understanding that the discussion is also applicable with respect to coupling the second drive motor 518 with the main shaft/end effector assembly 502.

The torque transmitted into the main shaft/end effector assembly 502 (Tc) by the first output link 530 can be calculated by Equation (1).

$$Tc = Tm \times P \times (N_{1B}/N_{1A}) \times (N_{1D}/N_{1C}) \qquad \text{Equation (1)}$$

where: Tm=Motor 1 drive torque
P=gear ratio for planetary gearbox P1
$N_{1A}$=number of gear teeth for gear 1A
$N_{1B}$=number of gear teeth for gear 1B
$N_{1C}$=number of gear teeth for gear 1C
$N_{1D}$=number of gear teeth for gear 1D The counteracting torque transmitted into the main shaft 508 (Tr) via the first base link 532 and the first rotational coupling 522 can be calculated by Equation (2).

$$Tr = -Tm \times (P-1) \times (N_{3B}/N_{3A}) \times (N_{3D}/N_{3C}) \qquad \text{Equation (2)}$$

where: $N_{3A}$=number of gear teeth for gear 3A
$N_{3B}$=number of gear teeth for gear 3B
$N_{3C}$=number of gear teeth for gear 3C
$N_{3D}$=number of gear teeth for gear 3D Decoupling of End Effector Drive Shaft Position from Main Shaft Position In addition to providing a counteracting torque as described above, the surgical assembly 500 and the instrument assembly 600 can be implemented to substantially decouple the position of the end effector drive shafts from the position of the main shaft. For example, the configuration of the surgical assembly 500 can be selected such that when the first and second input links 528, 534 are not rotating (i.e., the first and second drive motors 516, 518 are not rotating), a rotation of the main shaft 508 by the main shaft drive 504 will not cause a significant amount of rotation of the first and second drive shafts 542, 546 relative to the main shaft 508. The induced rotation of the first and second drive shafts 542, 546 can be less than 10 percent of the rotation of the main shaft 508. And in some embodiments, the induced rotation of the first and second drive shafts 542, 546 can be less than 5 percent of the rotation of the main shaft. This attribute is very beneficial. For example, in some embodiments the first and second drive motors 516, 518 have limited range of motion. By substantially decoupling the position of the first and second drive shafts 542, 546 from the position of the main shaft 508, the main shaft range of motion is not limited by the limited range of motion of the first and second drive motors 516, 518. Moreover, such decoupling is beneficial relative to the operating characteristics of the end effector with regard to the first and second rotary mechanisms 512, 514 as such decoupling prevents substantial actuation of the first and second rotary mechanisms 512, 514 in response to mere rotation of the main shaft. For example, where one of the first and second rotary mechanisms 512, 514 is used to actuate a stapler mechanism, the decoupling helps to prevent inadvertent firing of staples due to rotation of the first and second rotary mechanisms 512, 514 induced by rotation of the main shaft 508. Moreover, in the absence of such decoupling, it might be necessary to monitor the position of the main shaft 508 and use the monitored position to generate counteracting rotations of the first and second drive motors 516, 518 so as to correct for induced motion of the first and second drive shafts 542, 546.

The amount of rotation of the first drive shaft 542 induced by a rotation of the main shaft 508 can be calculated by Equation (3). As can be appreciated, parameters corresponding to the second drive shaft 546 can be substituted for the parameters corresponding to the first drive shaft 542 in Equation (3) to calculate the amount of rotation of the second drive shaft 546 induced by a rotation of the main shaft 508.

$$Ind_{rot} = Main_{rot} \times \left( \frac{\left(\frac{N_{3B}}{N_{3A}}\right) \times \left(\frac{N_{3D}}{N_{3C}}\right) \times \left(\frac{P-1}{P}\right) \times \left(\frac{N_{1A}}{N_{1B}}\right) \times \left(\frac{N_{1C}}{N_{1D}}\right) - 1}{\left(\frac{N_{1F}}{N_{1E}}\right)} \right) \quad \text{Equation (3)}$$

where: $N_{1E}$=number of gear teeth for gear 1E
$N_{1F}$=number of gear teeth for gear 1F Tables 1 through 3 list gearing parameters, resulting unit torque calculations, and levels of induced rotation for an end effector drive shaft for example embodiments.

TABLE 1

First Example Embodiment

| Parameter Description | Parameter Variable | Parameter Value |
| --- | --- | --- |
| Motor 1 output torque | Tm | 1 |
| Gear ratio for planetary gearbox P1 | P | 25 |
| Number of teeth for gear 1A | $N_{1A}$ | 32 |
| Number of teeth for gear 1B | $N_{1B}$ | 40 |
| Number of teeth for gear 1C | $N_{1C}$ | 23 |
| Number of teeth for gear 1D | $N_{1D}$ | 55 |
| Number of teeth for gear 1E | $N_{1E}$ | 43 |
| Number of teeth for gear 1F | $N_{1F}$ | 13 |
| Resulting input drive torque | Tc | 74.7 |
| Number of teeth for gear 3A | $N_{3A}$ | 50 |
| Number of teeth for gear 3B | $N_{3B}$ | 64 |
| Number of teeth for gear 3C | $N_{3C}$ | 23 |
| Number of teeth for gear 3D | $N_{3D}$ | 55 |
| Resulting counteracting torque | Tr | −73.5 |
| Percent torque imbalance | ((Tc + Tr)/Tc)/100 | 1.7 percent |
| Ref. Main Shaft Rotation | $Main_{rot}$ | 520 degrees |
| Induced End Effector Drive Shaft Rotation | $Ind_{rot}$ | −25.3 degrees (4.9 percent) |

TABLE 2

Second Example Embodiment

| Parameter Description | Parameter Variable | Parameter Value |
| --- | --- | --- |
| Motor 1 output torque | Tm | 1 |
| Gear ratio for planetary gearbox P1 | P | 9 |
| Number of teeth for gear 1A | $N_{1A}$ | 24 |
| Number of teeth for gear 1B | $N_{1B}$ | 54 |
| Number of teeth for gear 1C | $N_{1C}$ | 23 |
| Number of teeth for gear 1D | $N_{1D}$ | 55 |
| Number of teeth for gear 1E | $N_{1E}$ | 43 |
| Number of teeth for gear 1F | $N_{1F}$ | 13 |
| Resulting input drive torque | Tc | 48.4 |

TABLE 2-continued

Second Example Embodiment

| Parameter Description | Parameter Variable | Parameter Value |
| --- | --- | --- |
| Number of teeth for gear 3A | $N_{3A}$ | 51 |
| Number of teeth for gear 3B | $N_{3B}$ | 61 |
| Number of teeth for gear 3C | $N_{3C}$ | 14 |
| Number of teeth for gear 3D | $N_{3D}$ | 70 |
| Resulting counteracting torque | Tr | −47.8 |
| Percent torque imbalance | ((Tc + Tr)/Tc)/100 | 1.2 percent |
| Ref. Main Shaft Rotation | $Main_{rot}$ | 520 degrees |
| Induced End Effector Drive Shaft Rotation | $Ind_{rot}$ | −20.6 degrees (4.0 percent) |

TABLE 3

Third Example Embodiment

| Parameter Description | Parameter Variable | Parameter Value |
| --- | --- | --- |
| Motor 1 output torque | Tm | 1 |
| Gear ratio for planetary gearbox P1 | P | 25 |
| Number of teeth for gear 1A | $N_{1A}$ | 23 |
| Number of teeth for gear 1B | $N_{1B}$ | 56 |
| Number of teeth for gear 1C | $N_{1C}$ | 23 |
| Number of teeth for gear 1D | $N_{1D}$ | 55 |
| Number of teeth for gear 1E | $N_{1E}$ | 43 |
| Number of teeth for gear 1F | $N_{1F}$ | 13 |
| Resulting input drive torque | Tc | 145.6 |
| Number of teeth for gear 3A | $N_{3A}$ | 51 |
| Number of teeth for gear 3B | $N_{3B}$ | 61 |
| Number of teeth for gear 3C | $N_{3C}$ | 14 |
| Number of teeth for gear 3D | $N_{3D}$ | 70 |
| Resulting counteracting torque | Tr | −143.5 |
| Percent torque imbalance | ((Tc + Tr)/Tc)/100 | 1.4 percent |
| Ref. Main Shaft Rotation | $Main_{rot}$ | 520 degrees |
| Induced End Effector Drive Shaft Rotation | $Ind_{rot}$ | −24.0 degrees (4.6 percent) |

Related Methods

Figure 31:
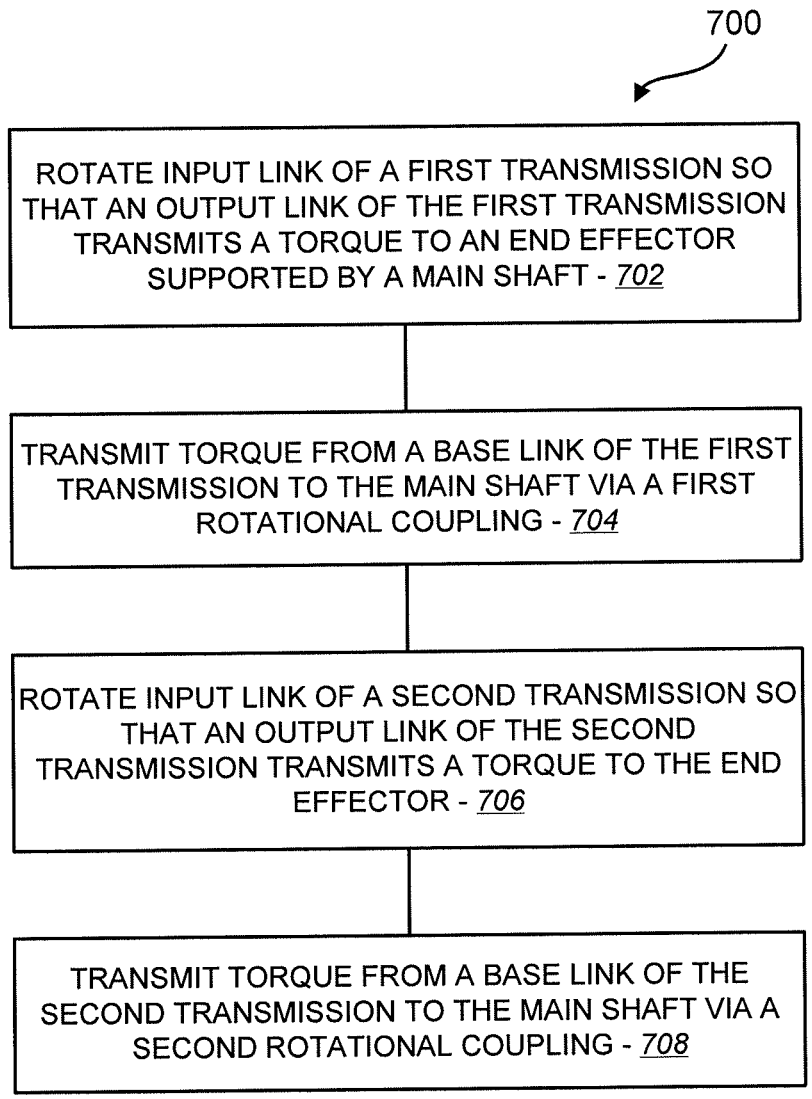
FIG. 31 is a flow diagram of a method for preventing an actuation torque transmitted to an end effector from rotationally driving a back-drivable main shaft during surgery, in accordance with many embodiments.

FIG. 31 illustrates a method 700 for preventing an actuation torque transmitted to an end effector from back driving a back-drivable main shaft during surgery, in accordance with many embodiments. The above surgical assembly 500 and the instrument assembly 600 described above can be used to practice the method 700. And one or more of the following acts can be omitted.

In act 702, a first input link of a first transmission is rotated so that a first output link of the first transmission transmits a first output torque to a main shaft assembly that includes a main shaft and an end effector supported by the main shaft and transmits a first end effector torque to the end effector. The first transmission provides a first gear ratio between the first input link and the first output link. The first output torque is greater than a back-driving torque threshold for a main shaft drive that is operable to rotationally drive the main shaft assembly.

In act 704, torque is transmitted from a first base link of the first transmission to the main shaft via a first rotational coupling. The first rotational coupling provides a second gear ratio between the first base link and the main shaft such that a first counteracting torque is applied to the main shaft that is opposite in direction to the first output torque. The first counteracting torque inhibits rotational driving of the main shaft assembly by the first output torque.

The main shaft drive may have a back-driving torque threshold such that the main shaft back drives the main shaft drive when the main shaft assembly is subject to a net torque over the back-driving torque threshold and does not back drive the main shaft drive when the main shaft assembly is subject to a net torque under the back-driving torque threshold. Preferably, the magnitude of the first counteracting torque differs from the magnitude of the first output torque by a first net torque magnitude that is less than 50 percent of the back-driving torque threshold. More preferably, the first net torque magnitude is less than 25 percent of the back-driving torque threshold, even when the first output torque exceeds the back-driving torque threshold. More preferably still, the first net torque magnitude is less than 10 percent of the back-driving torque threshold, even when the first end effector torque exceeds the back-driving torque threshold. And ideally, the first net torque magnitude is less than 2 percent of the back-driving torque threshold, even when the first end effector torque exceeds the back-driving torque threshold.

In act 706, a second input link of a second transmission is rotated so that a second output link of the second transmission transmits a second output torque to the main shaft assembly and transmits a second end effector torque to the end effector. The second transmission provides a third gear ratio between the second input link and the second output link. The second output torque link is greater than the back-driving torque threshold for the main shaft drive.

In act 708, torque is transmitted from a second base link of the second transmission to the main shaft via a second rotational coupling. The second rotational coupling provides a fourth gear ratio between the second base link and the main shaft such that a second counteracting torque is applied to the main shaft that is opposite in direction to the second output torque. The second counteracting torque inhibits rotational driving of the main shaft assembly by the second output torque.

The first and second rotational couplings can share one or more common components. For example, the first and second rotational couplings can share a common drive shaft.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A minimally invasive robotic surgical assembly comprising:
   a base;
   a main shaft assembly rotationally mounted to the base, the main shaft assembly including a main shaft, an end effector supported by the main shaft, and a first end effector drive shaft drivingly coupled to the end effector;
   a main shaft drive rotationally driving the main shaft relative to the base;
   a first input drive shaft transmitting a first input torque; and
   a first transmission having a first input link rotationally coupled to the first input drive shaft, a first output link rotationally coupled with the first end effector drive shaft, and a first base link, the first transmission providing a first gear ratio between the first input link and the first output link so as to transmit a first output torque to the main shaft assembly in response to the first input torque, a first end effector torque being transmitted by the first end effector drive shaft to the end effector in response to the first output torque, the first base link rotationally coupled with the main shaft by a second gear ratio such that the first base link, in response to the first input torque, transmits a first counteracting torque to the main shaft that is opposite in direction from the first output torque such that the first counteracting torque inhibits rotational driving of the main shaft assembly by the first output torque.

2. The surgical assembly of claim 1, wherein the first counteracting torque has a magnitude that is within 10 percent of a magnitude of the first output torque.

3. The surgical assembly of claim 2, wherein the magnitude of the first counteracting torque is within 2 percent of the magnitude of the first output torque.

4. The surgical assembly of claim 1, wherein the first output link is coupled with the first end effector drive shaft via a rotational coupling providing a non-unity gear ratio.

5. The surgical assembly of claim 1, wherein the main shaft assembly has a back-driving torque threshold such that the main shaft back drives the main shaft drive when the main shaft assembly is subject to a net torque over the back-driving torque threshold and does not back drive the main shaft drive when the main shaft assembly is subject to a net torque under the back-driving torque threshold, the first counteracting torque having a magnitude that differs from a magnitude of the first output torque by a first net torque magnitude that is less than the back-driving torque threshold.

6. The surgical assembly of claim 5, wherein the first net torque magnitude is less than 50 percent of the back-driving torque threshold.

7. The surgical assembly of claim 6, wherein the first net torque magnitude is less than 25 percent of the back-driving torque threshold.

8. The surgical assembly of claim 7, wherein the first net torque magnitude is less than 10 percent of the back-driving torque threshold.

9. The surgical assembly of claim 1, wherein the first transmission comprises a first planetary gear box having a first sun gear, a first ring gear, and first planetary gears supported by a first carrier.

10. The surgical assembly of claim 9, wherein the first sun gear corresponds to the first input link, the first carrier corresponds to the first output link, and the first ring gear corresponds to the first base link.

11. The surgical assembly of claim 9, wherein the first carrier corresponds to the first input link, the first sun gear corresponds to the first output link, and the first ring gear corresponds to the first base link.

12. The surgical assembly of claim 9, wherein the first carrier or the first sun gear corresponds to the first base link.

13. The surgical assembly of claim 1, wherein a rotation of the main shaft induces a rotation of the first end effector drive shaft that is less than 10 percent of the rotation of the main shaft.

14. The surgical assembly of claim 13, wherein the induced rotation of the first end effector drive shaft is less than 5 percent of the rotation of the main shaft.

15. The surgical assembly of claim 1, further comprising:
a second end effector drive shaft drivingly coupled to the end effector and included in the main shaft assembly;
a second input drive shaft transmitting a second input torque; and
a second transmission having a second input link rotationally coupled to the second input drive shaft, a second output link rotationally coupled to the second end effector drive shaft, and a second base link, the second transmission providing a third gear ratio between the second input link and the second output link so as to transmit a second output torque to the main shaft assembly in response to the second input torque, a second end effector torque being transmitted by the second end effector drive shaft to the end effector in response to the second output torque, the second base link rotationally coupled with the main shaft by a fourth gear ratio such that the second base link, in response to the second input torque, transmits a second counteracting torque to the main shaft that is opposite in direction from the second output torque such that the second counteracting torque inhibits rotational driving of the main shaft assembly by the second output torque.

16. The surgical assembly of claim 15, wherein the second counteracting torque has a magnitude that is within 10 percent of a magnitude of the second output torque.

17. The surgical assembly of claim 16, wherein the magnitude of the second counteracting torque is within 2 percent of the magnitude of the second output torque.

18. The surgical assembly of claim 15, wherein the second output link is coupled with the second end effector drive shaft via a rotational coupling providing a non-unity gear ratio.

19. The surgical assembly of claim 15, comprising a common drive shaft through which the first and second base links are rotationally coupled with the main shaft.

20. The surgical assembly of claim 15, wherein the main shaft assembly has a back-driving torque threshold such that the main shaft back drives the main shaft drive when the main shaft assembly is subject to a net torque over the back-driving torque threshold and does not back drive the main shaft drive when the main shaft assembly is subject to a net torque under the back-driving torque threshold, of the second counteracting torque having a magnitude that differs from a magnitude of the second output torque by a second net torque magnitude that is less than the back-driving torque threshold.

21. The surgical assembly of claim 20, wherein the second net torque magnitude is less than 50 percent of the back-driving torque threshold.

22. The surgical assembly of claim 21, wherein the second net torque magnitude is less than 25 percent of the back-driving torque threshold.

23. The surgical assembly of claim 22, wherein the second net torque magnitude is less than 10 percent of the back-driving torque threshold.

24. The surgical assembly of claim 15, wherein the second transmission comprises a second planetary gear box having a second sun gear, a second ring gear, and second planetary gears supported by a second carrier.

25. The surgical assembly of claim 24, wherein the second sun gear corresponds to the second input link, the second carrier corresponds to the second output link, and the second ring gear corresponds to the second base link.

26. The surgical assembly of claim 24, wherein the second carrier corresponds to the second input link, the second sun gear corresponds to the second output link, and the second ring gear corresponds to the second base link.

27. The surgical assembly of claim 24, wherein the second carrier or the second sun gear corresponds to the second base link.

28. The surgical assembly of claim 24, wherein the first transmission comprises a first planetary gear box having a first sun gear, a first ring gear, and first planetary gears supported by a first carrier.

29. The surgical assembly of claim 28, wherein the first sun gear corresponds to the first input link, the first carrier corresponds to the first output link, and the first ring gear corresponds to the first base link.

30. The surgical assembly of claim 28, wherein the first carrier corresponds to the first input link, the first sun gear corresponds to the first output link, and the first ring gear corresponds to the first base link.

31. A method for preventing an actuation torque transmitted to an end effector from back driving a back-drivable main shaft during surgery, the method comprising:
rotating a first input link of a first transmission providing a first gear ratio between the first input link and a first output link of the first transmission, the first output link rotationally coupled with a main shaft assembly rotationally mounted to a base and including a main shaft and an end effector supported by the main shaft, a first output torque being transmitted by the first output link to the main shaft assembly and a first end effector torque being transmitted to the end effector in response to the first output torque, the first output torque being greater than a back-driving torque threshold for the main shaft assembly; and
transmitting torque from a first base link of the first transmission through a first rotational coupling between the first base link and the main shaft, the first rotational coupling providing a second gear ratio between the first base link and the main shaft such that a first counteracting torque is applied to the main shaft that is opposite in direction from the first output torque, the first counteracting torque inhibiting rotational driving of the main shaft assembly by the first output torque.

32. The method of claim 31, wherein the first net torque has a magnitude that is less than 50 percent of the back-driving torque threshold.

33. The method of claim 32, wherein the first net torque magnitude is less than 25 percent of the back-driving torque threshold.

34. The method of claim 33, wherein the first net torque magnitude is less than 10 percent of the back-driving torque threshold.

35. The method of claim 31, wherein the first counteracting torque has a magnitude that is within 10 percent of the magnitude of the first output torque.

36. The method of claim 35, wherein the magnitude of the first counteracting torque is within 2 percent of the magnitude of the first output torque.

37. The method of claim 31, wherein a first end effector drive shaft transmits the first end effector torque to the end effector and a rotation of the main shaft induces a rotation of the first end effector drive shaft that is less than 10 percent of the rotation of the main shaft.

38. The method of claim 37, wherein the induced rotation of the first end effector drive shaft is less than 5 percent of the rotation of the main shaft.

39. The method of claim 31, further comprising:
rotating a second input link of a second transmission providing a third gear ratio between the second input link and a second output link of the second transmission, the second output link rotationally coupled with the main shaft assembly so that a second output torque is transmitted by the second output link to the main shaft assembly and a second end effector torque is transmitted to the end effector in response to the second output torque, the second output torque being greater than the back-driving torque threshold; and transmitting torque from a second base link of the second transmission through a second rotational coupling between the second base link and the main shaft, the second rotational coupling providing a fourth gear ratio between the second base link and the main shaft such that a second counteracting torque is applied to the main shaft that is opposite in direction from the second output torque, the second counteracting torque inhibiting rotational driving of the main shaft assembly by the second output torque.

40. The The method of claim 39, wherein the first and second rotational couplings share a common drive shaft.

* * * * *